(12) United States Patent
Verkade et al.

(10) Patent No.: US 7,541,462 B2
(45) Date of Patent: Jun. 2, 2009

(54) TRIAMINOPHOSPHINE LIGANDS FOR CARBON-NITROGEN AND CARBON-CARBON BOND FORMATION

(75) Inventors: John G. Verkade, Ames, IA (US); Sameer Urgaonkar, Cambridge, MA (US); JuHua Xu, Minneapolis, MN (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 12/019,485

(22) Filed: Jan. 24, 2008

(65) Prior Publication Data
US 2008/0139806 A1 Jun. 12, 2008

Related U.S. Application Data

(62) Division of application No. 11/236,877, filed on Sep. 27, 2005, now Pat. No. 7,385,058.

(60) Provisional application No. 60/613,383, filed on Sep. 27, 2004.

(51) Int. Cl.
C07F 9/06 (2006.01)
(52) U.S. Cl. ............... 546/22; 564/12; 564/13; 564/14
(58) Field of Classification Search ............ 546/22; 564/12, 13, 14
See application file for complete search history.

(56) References Cited

U.S. PATENT DOCUMENTS

2005/0176978 A1  8/2005  Verkade et al.

OTHER PUBLICATIONS

B.L.Laube, R.D.Bertrand, G.A.Casedu. R.D.Compton, J.G.Verkade, Polycyclic Group V Ligands, III, Inorganic Chemistry, 1967, vol. 6, No. 1, pp. 173-176.*
S.Urgaonkar, M.Nagarajan, J.G.Verkade, P[N(i-Bu)CH2CH2]3N: A versatile ligand for the Pd-Catalyzed amination of aryl chlorides, Organic Letters, 2003, vol. 5, No. 6, pp. 815-818.*
U.S. Appl. No. 10/989,538, Restriction Requirement mailed Sep. 24, 2007, 7 pgs.
U.S. Appl. No. 11/236,877, Notice of Allowance mailed Dec. 27, 2007, 7 pgs.
U.S. Appl. No. 11/236,877 Non Final Office Action mailed Jul. 3, 2007, 7 pgs.
U.S. Appl. No. 11/236,877, Response filed Oct. 3, 2007 to Non-Final Office Action mailed Jul. 3, 2007., 8 pgs.
Clardy, J.C., et al., "Crystal and Molecular Structures of the Caged Amino Phosphorus Molecules OP(NMeCH$_2$)$_3$CMe and H$_3$BP(NMeCH$_2$)$_3$CMe", *Phosphorus*, 4(3), (1974), 133-141.
Cowley, A H., et al., "A UV Photoelectron Spectroscopic Investigation of Some Polycyclic Group VA Compounds and Related Acyclic Species. Part I: Free and Coordinated Aminophosphines and Related Compounds", *Inorg. Chem.*, 21, (1981),543-9.

Crochet, P., et al., "New Flouroionophores from Aniline Dimer Derivatives: a Variation of Cation Signalling Mechanism With the Number of Amino Groups", *Chem. Commun.*, (2000), 289-290.
De Silva, A. P., et al., "Signaling Recognition Events with Fluorescent Sensors and Switches", *Chem Rev.*, 97(5), School of Chemistry, Queen's University, Belfast BT9 5AG, Northern Ireland,(1997),1515-66.
Driver, MS., et al., "A Second-Generation Catalyst for Aryl Halide Amination: Mixed Secondary Amines from Aryl Halides and Primary Amines Catalyzed by (DPPF)PdCl$_2$", *Amer. Chem. Soc.*, 118(30), (Jul. 1996), 7217-7218.
Fleischer, E. B., et al., "Conversion of Aliphatic and Alicyclic Polyalcohols to the Corresponding Primary Polyamines, 36", *J. Org. Chem*, 36, (1971), 3042-3044.
Friedrich, M., et al., "Easy Access to Derivatives of 2-(Hydroxymethyl)propane-1,2,3-triol (Isoerythritol) with up to Four Separately Addressable Functionalities", *Journal of Organic Chemistry*, 34(39), (2003), 2138-2143.
Grasa, G., "Animation Reactions of Aryl Halides with Nitrogen Containing reagents Mediated by Palladium / Imidazolium Salt systems", *Journal of Organic Chemistry*, 66, (2001), 7729-7737.
Greco, G. E., et al., "Synthesis of Aryl-substituted Triamidoamine Ligands and Molybdenum (IV) Complexes that Contain Them", *Organomatallics*, 17(26), (1998), 5591-5593.
Hartwig, J. F., et al., "Room-Temperature Palladium-Catalyzed Amination of Aryl Bromides and Chlorides and Extended Scope of Aromatic C-N and Chlorides and Extended Scope of Aromatic C-N", *J. Org. Chem.*, 64, (1999), 5575-5580.
Hirano, T., et al., "Novel-Zinc Fluorescent Probes Excitable with Visible Light for Biological Applications", *Angew. Chem. Int. Ed.*, 39(6), (2000), 1052-1054.

(Continued)

*Primary Examiner*—Karl J. Puttlitz
*Assistant Examiner*—Sudhakar Katakam
(74) *Attorney, Agent, or Firm*—Schwegman, Lundberg & Woessner, P.A.; Michael H. Haukaas

(57) ABSTRACT

Methods and compounds are provided for the formation of carbon-nitrogen or carbon-carbon bonds comprising reacting an amine or an aryl boronic acid with an aryl halide in the presence of a palladium catalyst, a base, and a compound of formula II:

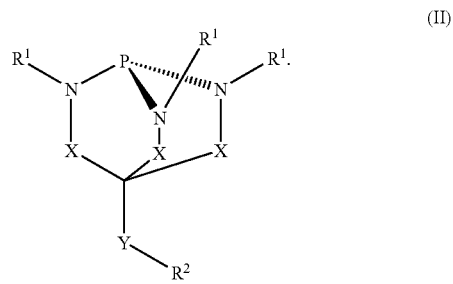

(II)

15 Claims, No Drawings

OTHER PUBLICATIONS

Kataoka, Noriyasu, et al., "Air Stable, Sterically Hindered Ferrocenyl Dialkylphosphines for Palladium-Catalyzed C-C, C-N, and C-O Bond-Forming Cross-Couplings", *J. Org. Chem.*, 67, (2002), 5553-5566.

Laube, B L., et al., "Polycyclic Group V Ligands. III. 2,6,7-Trimethyl-4methyl-2,6,7-friaza1-phosphabicyclo[2.2.2] octane. A Bidentate Donor", *Inorganic Chemistry*, 6, (Jan. 1967), 173-176.

Litke, Adam F., et al., "Versatile catalysts for the suzuki cross coupling of arylboronic acids with aryl and vinyl halides and triflates under mild conditions", *Journal of the American Chemical Society*, 122, (2000), 4020-4028.

Littke, Adam F., et al., "Palladium-catalyzed coupling reactions of aryl chlorides", *Angew. Chem. Int. Ed.*, 41, (2002), 4176-4211.

Lohr, H.-G., et al., "Chromo- and Fluoroionophores. A New Class of Dye Reagents", *Acc. Chem. Res.*, 18, (1985), 65-72.

Matsumoko, K., et al., "$Ag^+$ Ion-selective lariat ethers: high pressure syntheses and cation recognition properties", *J. Chem. Soc. Perkins Trans.*, (1995), 2497-2502.

Miyaura, N., et al., "Palladium-Catalyzed Cross-Coupling Reactions of Organoboron Compounds", *Chem. Rev.*, 95, (1995),2457-83.

Moloy, K. G., et al. "N-Pyrrolyl Phosphines: An Unexploited Class of Phosphine Ligands with Exceptional n-Acceptor Character", *J. Am. Chem. Soc.*, 117, (1995), 7696-7710.

Muci, A. R., et al., "Practical Palladium Catalysts for C-N and C-O Bond Formation", *Topics in Current Chemistry*, 219, (2002), 133-209.

Nishiyama, M., et al., "Synthesis of N-Arylpiperazines from Aryl Halides and Piperazine under a Palladium Tri-tert-butylphosphine Catalyst", *Tetrahedron Letters*, 39, (1998), 617-620.

Romming, C., et al., "Structural Studies on the Phosphorus-Nitrogen Bond. II. The Crystal Structure of Tris(morpholino)phosphine Selenide, Tris(piperidino)phosphine Selenide, and Tris(dimethylamino)-phosphine Selenide", *Acta Chemica Scandinavica A*, 33, (1979), 187-197.

Romming, C., et al., "Structural Studies on the Phosphorus-Nitrogen Bond. IV. The Crystal Structure of Ttris(morpholino)arsine. A Comparision With the Crystal Structure of Tri(morpholino)phosphine", *Acta Chemica Scandinavica A*, 34, (1980), 365-373.

Socol, S. M., et al., "Ligation of Phosphorous Ligands to Silver(1). 1. Coordination of One to Four $P(NR_2)_3$ Ligands and the Structure of a Nonlinear Two-Coordinate Complex", *Inorg. Chem.*, 23, (1984), 88-94.

Stanforth, S. P., "Catalytic Cross-coupling Reactions in Biaryl Synthesis", *Tetrahedron*, 54, (1998), 263-303.

Su, W., et al., "$Pd_2(dba)_3$/P($i$-BuNCH$_2$CH$_2$)$_3$N-Catalyzed Stille Cross-Coupling of Aryl Chlorides", *Organic Letters*, 6(9), (2004), 1421-1424.

Urgaonkar, S., et al., "Application of a New Bicyclic Triaminophosphine Ligand in Pd-Catalyzed Buchwald-Hartwig Amination Reactions of Aryl Chlorides, Bromides, and Iodides", *J. Org. Chem.*, 68, (2003), 8416-8423.

Urgaonkar, S., et al., "P($i$BuNCH$_2$CH$_2$)$_3$N: an Effective Ligand in the Palladium-Catalyzed Amination of Aryl Bromides and Iodides.", *Journal of Organic Chemistry*, 68(2), (2003), 452-459.

Urgaonkar, S., et al., "P[N($i$-Bu)CH$_2$CH$_2$]$_3$N: a Versatile Ligand for the Pd-Catalyzed Amination of Aryl Chlorides", *Organic Letters*, 5(6), (2003), 815-818.

Urgaonkar, S., et al., "Palladium/Proazaphosphatrane-Catalyzed Amination of Aryl Halides Possessing in a Phenol, Alcohol, Acetanilide, Amide or an Enolizable Ketone Functional Group:Efficacy of Lithium Bis(trimethylsilyl)amide as the Base", *Adv. Synth. Catal.*, 346, (2004), 611-616.

Urgaonkar, S., et al., "Pd/P($i$-BuNCH$_2$CH$_2$)$_3$ N: an Efficient Catalyst for Suzuki Cross-Coupling of Aryl Bromides and Chlorides with Arylboronic Acids", *Tetrahedron Letters*, 43, (2002), 8921-8924.

Urgaonkar, S., "Synthesis of N-aryl-aza-crown ethers via Pd-catalyzed amination reactions of aryl chlorides with aza-crown ethers", *Tetrahedron*, 60, (2004),11837-11842.

Verkade, J., "P(RNCH$_2$CH$_2$)$_3$N: Very Strong Non-Ionic Bases Useful in Organic Synthesis", *Topics in Current Chemistry*, 223, (2003), 3-40.

Verkade, J., et al., "Recent Applications of Proazaphosphatranes in Organic Synthesis", *Adrichema Acta*, 37(1), (2004),3-26.

Verkade, J., et al., "Triaminophosphate Ligands for Carbon-Nitrogen and Carbon-Carbon Bond Formation", U.S. Appl. No. 11/236,877, filed Sep. 27, 2005, 49 pgs.

Witulski, B. et al., "*N*-(9-Anthryi)aza-18-crown-6: Palladium-catalysed Synthesis, Photophysical Properties and Cation Binding Ability", *Tetrahedron Letters*, 39, (1998), 4807-4808.

Witulski, B., et al., "Novel Alkali Cation Chemosensors Based on *N*-9-Anthrylaza-crown Ethers", *Organic Letters*, 3(10), (2001),1467-1470.

Wolfe, J. P., et al., "Rational Development of Practical Catalysts for Aromatic Carbon-Nitrogen Bond Formation", *Acc. Chem. Res.*, 31, (1998), 805-818.

Wolfe, J. P., et al., "Room Temperature Catalytic Amination of Aryl Iodides", *J. Org. Chem.*, 62, (1997), 6066-6068.

Xi, S K., et al., "Bridgehead-Bridgehead Communication in Untransannulated ZP (ECH$_2$CH$_2$)$_3$N Systems", *Inorg. Chem.*, 29, (1989), 2214-2220.

You, et al., "A General Method for the Direct a-Arylation of Nitriles with Aryl Chlorides", *Angew. Chem. Int. Ed.*, 42, (2003),5051-5053.

You, J., et al., "P(i-BuNCH$_2$CH$_2$)$_3$N: An Efficient Ligand for the Direct α-Arylation of Nitriles with Aryl Bromides", *J. Org. Chem.*, 68, (2003), 8003-8007.

Zhang, X.-X., et al., "Efficient Synthesis of N-Aryl-Aza-Crown Ethers via Palladium-Catalyzed Amination", *J Org Chem.*, 65(23), (2000),8027-31.

\* cited by examiner

TRIAMINOPHOSPHINE LIGANDS FOR CARBON-NITROGEN AND CARBON-CARBON BOND FORMATION

CROSS-REFERENCE TO RELATED APPLICATIONS

This application is a divisional of U.S. patent application Ser. No. 11/236,877, filed Sep. 27, 2005, now U.S. Pat. No. 7,385,058 which claims priority under 35 U.S.C. 119(e) from U.S. Provisional Application No. 60/613,383, filed Sep. 27, 2004. These applications are incorporated herein by reference.

GOVERNMENT FUNDING

This invention was made with Government support under NSF Contract No. CHE-9905354. The United States Government has certain rights in this invention.

BACKGROUND

The synthesis of arylamines from amines and aryl halides or halide equivalents such as tosylates and triflates using palladium methodology has enjoyed considerable attention in the literature (Hartwig, J. F. In *Modern Amination Methods*; Ricci, A., Ed.; Wiley-VCH: Weinheim, Germany, 2000; Wolfe, J. P.; Wagaw, S.; Marcoux, J.-F.; Buchwald, S. L. *Acc. Chem. Res.* 1998, 31, 805). One reason for this attention is that arylamines possess a diverse range of potential applications in the pharmaceutical, dye, agricultural, and polymer industries. Aryl amines are also useful as ligands for transition metals (Greco, G. E.; Popa, A. I.; Schrock, R. R. *Organometallics* 1998, 17, 5591).

The chemistry of N-aryl-aza-crown ether derivatives is attracting significant interest because of the utility of these compounds to synthesize fluoroionophores in which, for example, a fluorescent aryl moiety is covalently linked to the nitrogen of an aza-crown ether (Lohr, H.-G.; Vogtle, F. *Acc. Chem. Res.* 1985, 18, 65; de Silva, et al. *Chem. Rev.* 1997, 97, 1515). These molecules can serve as sensitive and selective sensors of cations by binding them in the crown ether, thereby modifying the intensity and/or the energy of the signal of the fluorophore. Traditional approaches to the preparation of N-aryl-aza-crown ethers include nucleophilic aromatic substitution of activated aryl halides with aza-crown ethers under high pressure conditions (Matsumoto, et al. *J. Chem. Soc., Perkin Trans.* 1 1995, 2497), or manipulation of functional groups on aniline precursors (Crochet, et al. *Chem. Commun.* 2000, 289; and Hirano, et al. *Angew. Chem., Int. Ed.* 2000, 39, 1052). However, these approaches suffer from one or more of the following problems that impede accessibility to this important class of compounds: stringent conditions, multiple step syntheses, low yields, and limited substrate scope.

In recent years, palladium-catalyzed Buchwald-Hartwig amination reactions of aryl halides with amines have emerged as a method of choice for C—N bond forming processes (Muci, A. R.; Buchwald, S. L. *Top. Curr. Chem.* 2002, 219, 131). In this respect, Witulski et al. have developed a Pd/PPh$_3$ and a Pd/P(o-tol)$_3$ catalyst system for the coupling of aryl and heteroaryl bromides with aza-crown ethers (Witulski, et al. *Tetrahedron Lett.* 1998, 39, 4807; Witulski, et al. *Org. Lett.* 2001, 3, 1467). However, this method is limited to electron-poor aryl and heteroaryl bromides. Additionally, the use of P(t-Bu)$_3$, a popular ligand for Pd-catalyzed amination reactions, gave inferior results, probably because of its steric bulk (Hartwig, et al. *J. Org. Chem.* 1999, 64, 5575; Nishiyama, M.; Yamamoto, T.; Koie, Y. *Tetrahedron Lett.* 1998, 39, 617).

An improvement to the above protocol was described by Zhang and Buchwald (Zhang, X.-X.; Buchwald, S. L. *J. Org. Chem.* 2000, 65, 8027) who achieved cross-coupling of aryl bromides with aza-crown ethers using a catalyst system comprising Pd$_2$(dba)$_3$ and biphenyl-based monophosphine ligands with NaO-t-Bu as the base. Although electronically diverse and also ortho-substituted aryl bromides can be employed in these reactions, limitations still exist. For example, the authors noted that poor yields of N-aryl-aza-crown ethers were obtained when weak bases such as Cs$_2$CO$_3$ or K$_3$PO$_4$ were used in place of NaO-t-Bu, thus precluding the introduction of various base-sensitive functional groups into the aryl substrate. Another apparent limitation is that no examples employing aryl chlorides as the coupling partner were reported. Aryl chlorides are cheaper and are available in wider diversity than bromides or iodides, and their applicability in coupling with aza-crown ethers would constitute a significant advance, especially since aza-crown ethers are currently quite expensive.

Thus, ligands described in the literature that effect carbon-nitrogen bond formation often have drawbacks such as high cost, air and moisture instability, inability to effect a variety of transformations, difficulty employing acyclic secondary amines, lack of versatility in the amination reactions of aryl iodides, and requirement for high temperatures to aminate functionalized substrates (for example, substrates possessing ester and nitro functional groups). Despite current interest, there remains a need for novel ligand systems for the formation of carbon-nitrogen bonds.

Furthermore, palladium-catalyzed cross-coupling reactions of aryl halides with arylboronic acids to form biaryls are important transformations. Biaryls are important building blocks in the synthesis of many pharmaceutically active compounds, polymers, herbicides, liquid crystals, and ligands (Miyaura, N.; Suzuki, A. *Chem. Rev.* 1995, 95, 2458; Stanforth, S. P. *Tetrahedron* 1998, 54, 263). This cross-coupling reaction is known as the Suzuki-Miyaura reaction and is particularly useful because boron compounds present many advantages in relation to other organometallic compounds such as tin, magnesium, zinc, and silicon: commercial availability, minimal toxicity, and a wide range of functional group compatibility. Moreover, unlike other organometallic compounds, organoboron compounds are air- and moisture-stable reagents. Ancillary ligands on palladium play an important role in the efficiency of this reaction. Among various types of ligands, the most attention has been focused on electron-rich and sterically demanding alkyl phosphines (Little, A. F.; Dai, C.; Fu, G. C. *J. Am. Chem. Soc.* 2000, 122, 4020). Despite current interest, there remains a need for novel ligand systems for use in the Suzuki-Miyaura reaction.

SUMMARY OF THE INVENTION

The present invention provides a compound of formula I:

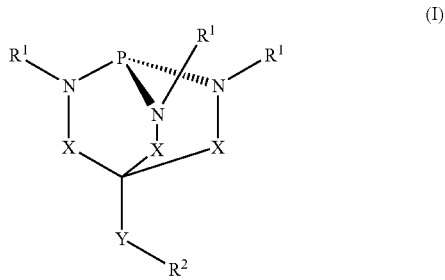

(I)

wherein each X is independently (CH$_2$)$_n$ and each n is independently 1-3;

Y is a single bond, O, $(C_1-C_8)$alkylene, $(C_5-C_{12})$arylene, carbonyl, oxycarbonyl, carbonyloxy, $NR_a$, or $S(O)_m$;

each $R^1$ is independently H, $(C_1-C_8)$alkyl, $(C_3-C_8)$cycloalkyl, $(C_3-C_8)$cycloalkyl$(C_1-C_6)$alkyl, $(C_1-C_8)$perfluoroalkyl, $(C_5-C_{12})$aryl, $(C_5-C_{12})$heteroaryl, $(C_5-C_{12})$heterocyclyl, $Si((C_1-C_6)$alkyl$)_3$, $Si((C_1-C_6)$alkoxy$)_3$, $Si((C_5-C_{12})$aryl$)_3$, or $Si((C_5-C_{12})$aryloxy$)_3$;

$R^2$ is H, $OR_a$, $(C_1-C_8)$alkyl, $(C_3-C_8)$cycloalkyl, $(C_3-C_8)$cycloalkyl$(C_1-C_6)$alkyl, $(C_1-C_8)$perfluoroalkyl, $(C_5-C_{12})$aryl, $(C_5-C_{12})$heteroaryl, $(C_5-C_{12})$heterocyclyl, $Si((C_1-C_6)$alkyl$)_3$, $Si((C_1-C_6)$alkoxy$)_3$, $Si((C_5-C_{12})$aryl$)_3$, $Si((C_5-C_{12})$aryloxy$)_3$, $NHR_a$, $N(R_a)_2$, halo, nitro, cyano, $S(O)_mOR_a$, $SO_3H$, or $P(O)_2OR_a$;

m is 0-2;

$R_a$ is H, $(C_1-C_6)$alkyl, $(C_1-C_6)$alkylcarbonyl, $(C_5-C_{12})$aryl, or $(C_5-C_{12})$aryloxy;

any alkyl can optionally be substituted with one to three halo, hydroxy, nitro, cyano, $(C_5-C_{12})$aryl, $(C_1-C_6)$alkoxy, trifluoromethyl, oxo, thioxo, or $NR_bR_c$ groups, wherein $R_b$ and $R_c$ are each independently hydrogen, $(C_1-C_6)$alkyl, or $C(=O)OR_d$ wherein $R_d$ is hydrogen or $(C_1-C_6)$alkyl;

any alkyl is optionally interrupted with one to three oxy, thio, amino, sulfinyl, or sulfonyl groups;

any alkyl is optionally partially unsaturated;

any aryl can optionally be substituted with one or more (e.g., 1-5) halo, hydroxy, nitro, cyano, $(C_1-C_6)$alkoxy, trifluoromethyl, oxo, $NR_bR_c$, or $C(O)OR_d$ groups;

provided that when $R^1$ is methyl —Y—$R^2$ is not hydrogen or $(C_1-C_6)$alkyl; and provided that when $R^1$ is hydrogen, —Y—$R^2$ is not hydrogen.

The group X can be $(CH_2)_3$, $(CH_2)_2$, or preferably $(CH_2)$. The groups X can be the same or different from each other. $R^1$ can be $(C_1-C_8)$alkyl, specifically $(C_1-C_4)$alkyl, or more specifically isobutyl. The group Y can be a single bond (e.g., it can be absent, thus attaching the bridgehead carbon to $R^2$), and $R^2$ can be methyl. In some embodiments, the group —Y—$R^2$ is not hydrogen or alkyl. The invention provides a compound that has the structure:

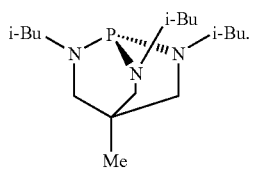

The invention also provides a method to aminate aryl halides, e.g., to form a carbon-nitrogen bond, to provide an aryl amine, the method comprising reacting an amine and an aryl halide in the presence of an effective amount of a palladium catalyst, a base, and a compound of formula II:

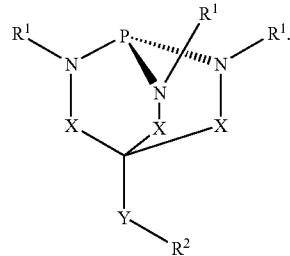

(II)

wherein
each X is independently $(CH_2)_n$ and each n is independently 1-3;

Y is a single bond, O, $(C_1-C_8)$alkylene, $(C_5-C_{12})$arylene, carbonyl, oxycarbonyl, carbonyloxy, $NR_a$, or $S(O)_m$;

each $R^1$ is independently H, $(C_1-C_8)$alkyl, $(C_3-C_8)$cycloalkyl, $(C_3-C_8)$cycloalkyl$(C_1-C_6)$alkyl, $(C_1-C_8)$perfluoroalkyl, $(C_5-C_{12})$aryl, $(C_5-C_{12})$heteroaryl, $(C_5-C_{12})$heterocyclyl, $Si((C_1-C_6)$alkyl$)_3$, $Si((C_1-C_6)$alkoxy$)_3$, $Si((C_5-C_{12})$aryl$)_3$, or $Si((C_5-C_{12})$aryloxy$)_3$;

$R^2$ is H, $OR_a$, $(C_1-C_8)$alkyl, $(C_3-C_8)$cycloalkyl, $(C_3-C_8)$cycloalkyl$(C_1-C_6)$alkyl, $(C_1-C_8)$perfluoroalkyl, $(C_5-C_{12})$aryl, $(C_5-C_{12})$heteroaryl, $(C_5-C_{12})$heterocyclyl, $Si((C_1-C_6)$alkyl$)_3$, $Si((C_1-C_6)$alkoxy$)_3$, $Si((C_5-C_{12})$aryl$)_3$, $Si((C_5-C_{12})$aryloxy$)_3$, $NHR_a$, $N(R_a)_2$, halo, nitro, cyano, $S(O)_mOR_a$, $SO_3H$, or $P(O)_2OR_a$;

m is 0-2;

$R_a$ is H, $(C_1-C_6)$alkyl, $(C_1-C_6)$alkylcarbonyl, $(C_5-C_{12})$aryl, or $(C_5-C_{12})$aryloxy;

any alkyl can optionally be substituted with one to three halo, hydroxy, nitro, cyano, $(C_5-C_{12})$aryl, $(C_1-C_6)$alkoxy, trifluoromethyl, oxo, thioxo, or $NR_bR_c$ groups, wherein $R_b$ and $R_c$ are each independently hydrogen, $(C_1-C_6)$alkyl, or $C(=O)OR_d$ wherein $R_d$ is hydrogen or $(C_1-C_6)$alkyl;

any alkyl is optionally interrupted with one to three oxy, thio, amino, sulfinyl, or sulfonyl groups;

any alkyl is optionally partially unsaturated;

any aryl can optionally be substituted with one or more (e.g., 1-5) halo, hydroxy, nitro, cyano, $(C_1-C_6)$alkoxy, trifluoromethyl, oxo, $NR_bR_c$, or $C(O)OR_d$ groups.

The group X can be $(CH_2)_3$, $(CH_2)_2$, or preferably $(CH_2)$. The groups X can be the same or different from each other. $R^1$ can be $(C_1-C_8)$alkyl, specifically $(C_1-C_4)$alkyl, or more specifically isobutyl. The group Y can be a single bond (e.g., it can be absent, thus attaching the bridgehead carbon to $R^2$), and $R^2$ can be methyl. The method can employ a compound that has the structure:

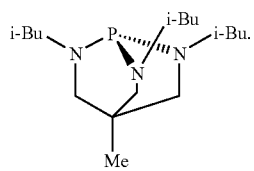

The method can employ any suitable and effective palladium catalyst. Preferably, the palladium catalyst is a Pd(0) reagent such as $Pd_2(dba)_3$ or a Pd(II) reagent that is reducible to Pd(0) such as $Pd(OAc)_2$. The base can be an organic or inorganic base, such as, e.g., an alkali metal carbonate or an alkali metal alkoxide. Specific examples include, but are not limited to, cesium carbonate and sodium tert-butoxide. The transition metal catalyst can be used stoichiometrically or catalytically. The compound of formula II can also be used stoichiometrically or catalytically. The reaction can be heated to a temperature of about 50° C. to about 120° C., specifically to about 70° C. to about 115° C., or more specifically to about 80° C. to about 110° C. Any suitable and effective solvent can be used. Preferably, the solvent is an aromatic solvent such as toluene. The method can be used to aminate aryl halides with aza-crown ethers to form N-aryl-aza-crown ethers.

The invention further provides a method to cross-couple aryl halides and aryl boronic acids to form biaryls, the method comprising reacting an aryl boronic acid and an aryl halide in the presence of an effective amount of a palladium catalyst, a base, and a compound of formula II:

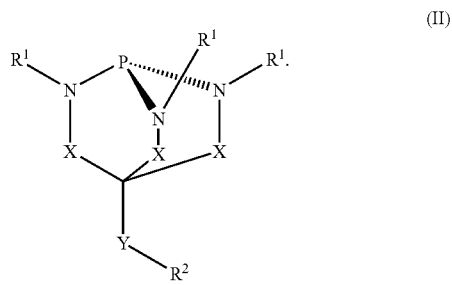

(II)

The group X can be $(CH_2)_3$, $(CH_2)_2$, or preferably $(CH_2)$. The groups X can be the same or different from each other. $R^1$ can be $(C_1-C_8)$alkyl, specifically $(C_1-C_4)$alkyl, or more specifically isobutyl. The group Y can be a single bond (e.g., it can be absent, thus attaching the quaternary carbon to $R^2$), and $R^2$ can be methyl. The method can employ a compound that has the structure:

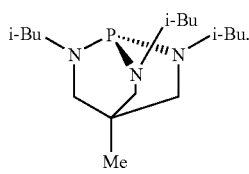

The method can employ any suitable and effective palladium catalyst. Preferably, the palladium catalyst is a Pd(0) reagent such as $Pd_2(dba)_3$ or a Pd(II) reagent that is reducible to Pd(0) such as $Pd(OAc)_2$. The base can be an organic or inorganic base, such as, e.g., an alkali metal carbonate or an alkali metal alkoxide. Specific examples include, but are not limited to, cesium carbonate or sodium tert-butoxide. The transition metal catalyst can be used stoichiometrically or catalytically. The compound of formula II can also be used stoichiometrically or catalytically. The reaction can be heated to a temperature of about 50° C. to about 120° C., specifically to about 70° C. to about 110° C., or more specifically to about 75° C. to about 85° C. Any suitable and effective solvent can be used. Preferably, the solvent is an aromatic solvent such as toluene. The method can be used to cross-couple aryl halides and aryl boronic acids to form biaryl compounds.

DETAILED DESCRIPTION OF THE INVENTION

The following definitions are used, unless otherwise described: halo is fluoro, chloro, bromo, or iodo. Alkyl, alkoxy, alkenyl, etc. denote both straight and branched groups; but reference to an individual radical such as "propyl" embraces only the straight chain radical, a branched chain isomer such as "isopropyl" being specifically referred to. Aryl denotes an optionally substituted phenyl radical or an optionally substituted ortho-fused bicyclic carbocyclic radical having about nine to ten ring atoms in which at least one ring is aromatic.

It will be appreciated by those skilled in the art that compounds useful in the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound useful in the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antibacterial activity using the standard tests described herein, or using other similar tests which are well known in the art.

Specific and preferred values listed below for radicals, substituents, and ranges, are for illustration only; they do not exclude other defined values or other values within defined ranges for the radicals and substituents The group $(C_1-C_8)$alkyl refers to a linear or branched hydrocarbon that is optionally substituted with functional groups as described herein. Specifically, $(C_1-C_8)$alkyl can be methyl, ethyl, propyl, isopropyl, butyl, iso-butyl, sec-butyl, tert-butyl, pentyl, 3-pentyl, hexyl, heptyl, or octyl; partially unsaturated $(C_2-C_6)$alkyl or $(C_2-C_6)$alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_1-C_5)$alkanoyl can be carbonyl, acetyl, propanoyl, butanoyl, isopropanoyl, or pentenoyl; $(C_1-C_6)$alkoxy can be methoxy, ethoxy, propoxy, isopropoxy, butoxy, iso-butoxy, sec-butoxy, pentoxy, 2-pentoxy, 3-pentoxy, or hexyloxy; halo$(C_1-C_6)$alkoxy can be trifluoromethyloxy, 2-chloroethyloxy, 3,3-dichloropropyloxy, or 4,4,4-trifluorobutyloxy; $(C_3-C_8)$cycloalkyl can be cyclopropyl, cyclobutyl, cyclopentyl, cyclohexyl, cycloheptyl, or cyclooctyl; $(C_3-C_8)$cycloalkyloxy can be cyclopropyloxy, cyclobutyloxy, cyclopentyloxy, cyclohexyloxy, cycloheptyloxy, or cyclooctyloxy; hydroxy$(C_1-C_6)$alkoxy can be hydroxymethoxy, 1-hydroxyethoxy, 2-hydroxyethoxy, 1-hydroxypropoxy, 2-hydroxypropoxy, 3-hydroxypropoxy, 1-hydroxybutoxy, 4-hydroxybutoxy, 1-hydroxypentoxy, 5-hydroxypentoxy, 1-hydroxyhexoxy, or 6-hydroxyhexoxy; $(C_1-C_6)$alkoxycarbonyl can be methoxycarbonyl, ethoxycarbonyl, propyloxycarbonyl, isopropyloxycarbonyl, 2-methylpropyloxycarbonyl, butyloxycarbonyl, pentyloxycarbonyl, or hexyloxycarbonyl; $(C_1-C_6)$alkanoyloxy can be carbonyloxy, acetyloxy, propanoyloxy, butanoyloxy, 2-methylpropanoyloxy, 2-methylbutanoyloxy, 3-methylbutanoyloxy, pentanoyloxy, or hexanoyloxy.

The terms "alkylene" and "arylene" refer to a diradical of an alkyl group and an aryl group, respectively.

The term "partially unsaturated" refers to a linear or branched hydrocarbon having one or more carbon-carbon double bonds, one or more carbon-carbon triple bonds, or both.

When a group is referred to as a single bond, that group is considered absent or alternatively part of the bond joining the groups attached thereto.

Combinations of substituents and/or variables are permissible only if such combinations result in stable compounds. A "stable compound" herein refers to a compound that is sufficiently robust to survive isolation to a useful degree of purity from a reaction mixture.

Compounds of the invention can also include optional protecting groups. Suitable protecting groups are known to those skilled in the art (see for example, T. W. Greene, *Protecting Groups In Organic Synthesis*; Wiley: New York, Third Edition, 1999, and references cited therein).

"Aryl" means a monovalent aromatic hydrocarbon radical of 6-20 carbon atoms derived by the removal of one hydrogen atom from a single carbon atom of a parent aromatic ring system. Aryl groups are typically made up of 6-10 carbon atoms and can optionally possess additional substituents. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl, and the like. The arylalkyl group can include 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O—)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen (F, Cl, Br, or I); and each R is independently —H, alkyl, aryl, heterocycle, or a protecting group. Alkylene, alkenylene, alkynylene, and arylene groups may also be similarly substituted.

"Heterocycle" as used herein includes by way of example and not limitation the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo[5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

Useful sources of Pd catalyst include Pd(0) catalysts, for example, Pd$_2$(dba)$_3$, bis-(dibenzylideneacetone)palladium (0), bis(isonitrile)palladium(0), Pd(PPh$_3$)$_4$ [tetrakis(triphenylphosphine)palladium(0)], bis-(cyclohexylisonitrile) palladium(0), bis-(isopropylisonitrile)palladium(0), bis(tert.-butylisonitrile)palladium(0), bis-(p-tolylisonitrile)palladium(0), and bis-(p-methoxyphenyl isonitrile)palladium(0). Other Pd-containing compounds, e.g., Pd(II) compounds, can also be used in the present method. These include PdCl$_2$, palladium(II) carboxylate salts, such as Pd(OAc)$_2$, PdBr$_2$, Pd(CN)$_2$, Pd(NO$_3$)$_2$, PdSO$_4$, and the like. Other Pd catalysts which can be used in the present method include those disclosed in Blaser et al. (U.S. Pat. No. 4,335,054) at Col. 6, line 5 to Col. 7, line 3.

Bases used in the present process can be inorganic or organic bases, which are adequately soluble in the reaction medium. Representative bases are disclosed by Blaser et al. at Col. 7, lines 8-65 (U.S. Pat. No. 4,335,054). Inorganic bases for use in the present process include carbonates and bicarbonates, i.e., Na$_2$CO$_3$, KHCO$_3$, Li$_2$CO$_3$, K$_2$CO$_3$, NaHCO$_3$, CaCO$_3$, and the like. Useful organic bases include alkoxides such as potassium t-butoxide, acetates such as sodium and potassium acetate, and tertiary amines such as triethylamine and diisopropyl(ethyl)amine. Preferably, inorganic bases or alkoxide bases are used. Any suitable and effective ratio of base to aryl halide can be used. Preferably, the base is in excess with respect to the aryl halide. The mole ratio of the base to the aryl halide can be about 1-3:1, specifically about 1.1-2:1, and more specifically about 1.5:1.

Any suitable and effective solvent system can be used. Useful organic solvents include benzene, toluene, tetrahydrofuran (THF), dioxane, alkyl ethers, glycol ethers such as dimethoxyethane (DME), dimethylsulfoxide, dimethylformamide (DMF), acetonitrile, dimethylacetamide, and hexamethylphosphoramide (HMPA), and combinations of these solvents, optionally with minor amounts (e.g., 0.1 mol % to about 5 mol %) of water, as compatible.

Advantages of the new triaminophosphine ligands described herein include a high degree of air and moisture stability, and that a suitable palladium source (for example, Pd(OAc)$_2$ or Pd$_2$(dba)$_3$) can be used in combination with the triaminophosphine. This catalyst system provides the most efficient, general, and mild catalytic combination reported to date for the amination of aryl iodides. Also, this catalyst system can also be used for the amination of aryl bromides and aryl chlorides, and in forming carbon-carbon bonds between aryl boronic acids and aryl halides by displacement of the halide and boronic acid moieties (the Suzuki-Miyaura reaction). The reactions can accommodate a variety of base-sensitive functional groups such as nitro, ester, and cyano, when a weak base such as $Cs_2CO_3$ is employed (rather than the strong bases generally required in these transformations). The amination of functionalized substrates can be performed at lower temperature than is generally used in carbon-nitrogen formation reactions.

The present invention provides a novel compound of formula I:

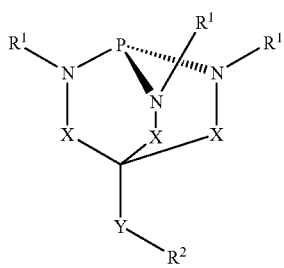

(I)

wherein each X is independently $(CH_2)_n$ and each n is independently 1-3;

Y is a single bond, O, $(C_1-C_8)$alkylene, $(C_5-C_{12})$arylene, carbonyl, oxycarbonyl, carbonyloxy, $NR_a$, or $S(O)_m$, wherein m is 0-2;

each $R^1$ is independently H, $(C_1-C_8)$alkyl, $(C_3-C_8)$cycloalkyl, $(C_3-C_8)$cycloalkyl$(C_1-C_6)$alkyl, $(C_1-C_8)$perfluoroalkyl, $(C_5-C_{12})$aryl, $(C_5-C_{12})$heteroaryl, $(C_5-C_{12})$heterocyclyl, $Si((C_1-C_6)alkyl)_3$, $Si((C_1-C_6)alkoxy)_3$, $Si((C_5-C_{12})aryl)_3$, or $Si((C_5-C_{12})aryloxy)_3$;

$R^2$ is H, $OR_a$, $(C_1-C_8)$alkyl, $(C_3-C_8)$cycloalkyl, $(C_3-C_8)$cycloalkyl$(C_1-C_6)$alkyl, $(C_1-C_8)$perfluoroalkyl, $(C_5-C_{12})$aryl, $(C_5-C_{12})$heteroaryl, $(C_5-C_{12})$heterocyclyl, $Si((C_1-C_6)alkyl)_3$, $Si((C_1-C_6)alkoxy)_3$, $Si((C_5-C_{12})aryl)_3$, $Si((C_5-C_{12})aryloxy)_3$, $NHR_a$, $N(R_a)_2$, halo, nitro, cyano, $S(O)_mOR_a$, $SO_3H$, or $P(O)_2OR_a$;

$R_a$ is H, $(C_1-C_6)$alkyl, $(C_1-C_6)$alkylcarbonyl, $(C_5-C_{12})$aryl, or $(C_5-C_{12})$aryloxy;

any alkyl can optionally be substituted with one to three halo, hydroxy, nitro, cyano, $(C_5-C_{12})$aryl, $(C_1-C_6)$alkoxy, trifluoromethyl, oxo, thioxo, or $NR_bR_c$ groups, wherein $R_b$ and $R_c$ are each independently hydrogen, $(C_1-C_6)$alkyl, or $C(=O)OR_d$ wherein $R_d$ is hydrogen or $(C_1-C_6)$alkyl;

any alkyl is optionally interrupted with one to three oxy, thio, amino, sulfinyl, or sulfonyl;

any alkyl is optionally partially unsaturated;

any aryl can optionally be substituted with one or more halo, hydroxy, nitro, cyano, $(C_1-C_6)$alkoxy, trifluoromethyl, oxo, $NR_bR_c$, or $C(O)OR_d$;

provided that when $R^1$ is methyl —Y—$R^2$ is not hydrogen or $(C_1-C_6)$alkyl; and provided that when $R^1$ is hydrogen, —Y—$R^2$ is not hydrogen.

The group X can be $(CH_2)_3$, $(CH_2)_2$, or preferably $(CH_2)$. The groups X can be the same or different from each other. $R^1$ can be $(C_1-C_8)$alkyl, specifically $(C_1-C_4)$alkyl, or more specifically isobutyl. The group Y can be a single bond (e.g., it can be absent, thus attaching the quaternary carbon to $R^2$), and $R^2$ can be methyl. The group X can also be substituted. The substituent can optionally form a ring that attaches X to Y, $R^1$, or $R^2$. The invention provides a compound that has the structure:

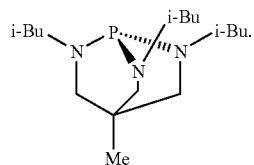

Various triaminophosphine ligands of formula I and II can be prepared according to conventional methods known to those of skill in the art. Convenient starting materials include isoerythitol (2-(hydroxymethyl)propane-1,2,3-triol) and its derivatives described by Friedrich, et al. (*Eur. J. Org. Chem.* 2003, 2138). In Scheme A below, the primary alcohol of A1 can be protected, and the sulfite protecting group can then be removed to afford triol A2. Protected triamine A3 can be prepared by amination of triol A2 (see Fleischer, E. B.; Gebala, A. E.; Levey, A.; Tasker, P. A. *J. Org. Chem.* 1971, 36, 3042). Triamine A3 can be converted to tri-$R^1$ compound A4 by nucleophilic displacements of halogens on groups such as $R^1$—Cl. Ring closure of A4 to triaminophosphine A5 can be achieved by heating the former in the presence of $P(NMe_2)_3$ at high temperature (for example, 175° C.) for a sufficient amount of time to afford A5. Removal of the alcohol protecting group followed by appropriate functional group transformations can afford compounds of formula III.

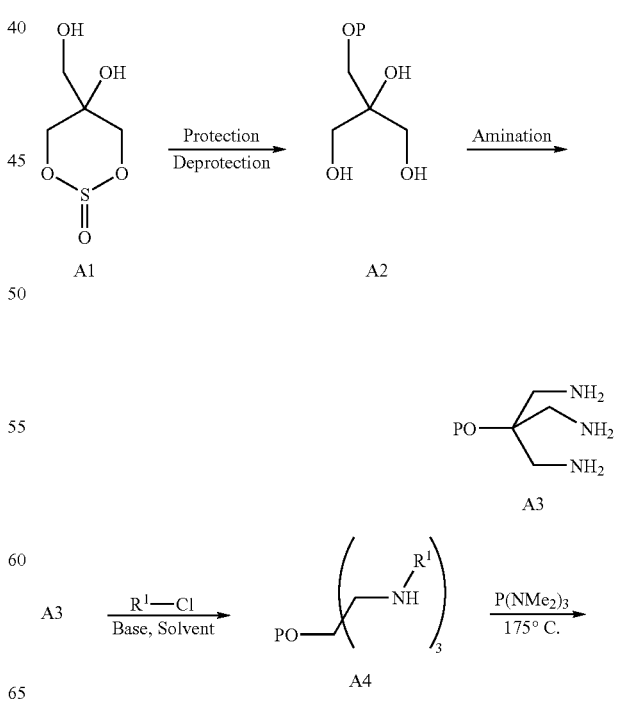

Scheme A

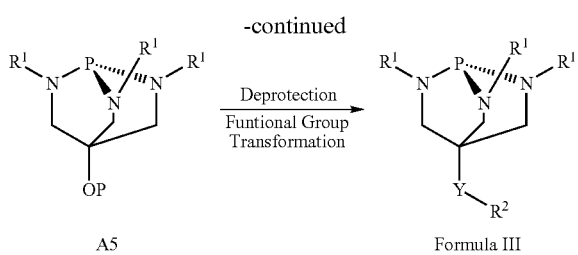

By employing variations of starting material A1, or alternatively, by modifying A1, other compounds of formula II can be prepared. Protecting groups may be necessary at various stages in the synthetic sequences, including when preparing alternative X groups for compounds of formula II. The use of various protecting groups is well known to those skilled in the art (see for example, T. W. Greene, *Protecting Groups In Organic Synthesis*; Wiley: New York, Third Edition, 1999, and references cited therein).

While the invention is described in conjunction with the enumerated claims, it will be understood that they are not intended to limit the invention to those claims. On the contrary, the invention is intended to cover all alternatives, modifications, and equivalents, which may be included within the scope of the present invention as defined by the claims. The invention will now be illustrated by the following non-limiting Examples.

EXAMPLES

Example 1

Synthesis of N-Aryl-Aza-Crown Ethers Via Pd-Catalyzed Amination Reactions of Aryl Chlorides with Aza-Crown Ethers The $Pd_2(dba)_3/P(i\text{-}BuNCH_2CH_2)_3N$ (1) catalyst system effectively catalyzes the coupling of aza-crown ethers with electronically diverse aryl chlorides, affording N-aryl-aza-crown ethers in good yields. The $Pd_2(dba)_3/P(i\text{-}BuNCH_2)_3$ CMe (2) catalyst system containing the more constrained bicyclic triaminophosphine is useful to couple aryl chlorides possessing base-sensitive ester, nitro, and nitrile functional groups.

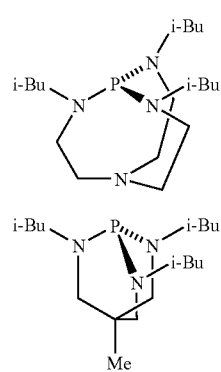

Recent explorations in palladium-catalyzed cross coupling reactions have established that electron-rich and commercially available proazaphosphatrane 1, serves as an excellent ligand in Suzuki, Buchwald-Hartwig amination, Stille, and alpha-arylation reactions. For Suzuki reactions, see Urgaonkar, S.; Nagarajan, M.; Verkade, J. G. *Tetrahedron Lett.* 2002, 43, 8921. For the Buchwald-Hartwig amination, see Urgaonkar, S.; Nagarajan, M.; Verkade, J. G. *J. Org. Chem.* 2003, 68, 452; Urgaonkar, S.; Nagarajan, M.; Verkade, J. G. *Org. Lett.* 2003, 5, 815; and Urgaonkar, S.; Verkade, J. G. *Adv. Synth. Catal.* 2004, 346, 611. For Stille reactions, see Su, W.; Urgaonkar, S.; Verkade, J. G. *Org. Lett.* 2004, 6, 1421. For alpha-arylation reactions, see You, J.; Verkade, J. G. *Angew. Chem., Int. Ed.* 2003, 42, 5051; You, J.; Verkade, J. G. *J. Org. Chem.* 2003, 68, 8003. Generally unreactive aryl chlorides can also be employed in these transformations. A new bicyclic triaminophosphine ligand 2 has also been developed that can be used in Buchwald-Hartwig amination reactions (Urgaonkar, S.; Xu, J-H.; Verkade, J. G. *J. Org. Chem.* 2003, 68, 8416). It is noted that ligand 2 is especially useful for substrates with functionalities that require a weak base such as $Cs_2CO_3$. In this example, the synthesis of a new ligand 2 is described, which though structurally similar to ligand 1, has quite different stereoelectronic properties.

Results and Discussion

Synthesis of ligand 2. The triaminophosphine ligand 2 was synthesized from triamine 4 as summarized in Scheme 1. Although commercially available (Fluka), 4 can be easily prepared in three high-yield steps from cheaper and commercially available 1,1,1-tris(hydroxymethyl)ethane (Fleischer, E. B.; Gebala, A. E.; Levey, A.; Tasker, P. A. *J. Org. Chem.* 1971, 36, 3042). Treatment of triamine 4 with isobutyryl chloride followed by $LiAlH_4$ reduction resulted in the formation of tri-iso-butyl substituted amine 5 in 81% yield in two steps. Ring closure of 5 to 2 was achieved by heating the former in the presence of $P(NMe_2)_3$ at 175° C. for 48 hours to afford 2 as a colorless liquid in 85% yield and in 69% overall yield from 4. Ligand 2 was unambiguously characterized by $^1H$, $^{13}C$, and $^{31}P$ NMR spectroscopy as well as elemental analysis (see Experimental section below). Remarkably, $^{31}P$ NMR spectroscopic monitoring of 2, kept in the air for 40 hours, revealed that about 90% of 2 remained unchanged.

Interestingly, $P(t\text{-}Bu)_3$, a highly effective ligand for wide variety of Pd-catalyzed cross-coupling reactions (Littke, A. F.; Fu, G. C. *Angew. Chem., Int. Ed.* 2002, 41, 4176), including amination reactions, has been shown to be destroyed in air within 2 hours (Wolfe, J. P.; Buchwald, S. L. *Angew. Chem., Int. Ed.* 1999, 38, 2413). Although ligand 2 showed a high degree of air and moisture stability, it is recommend that it is stored under argon.

Scheme 1

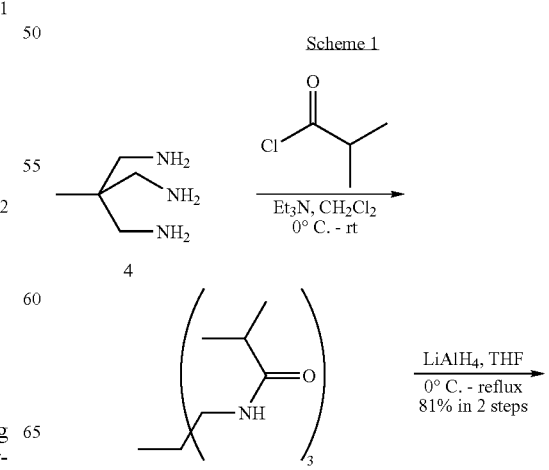

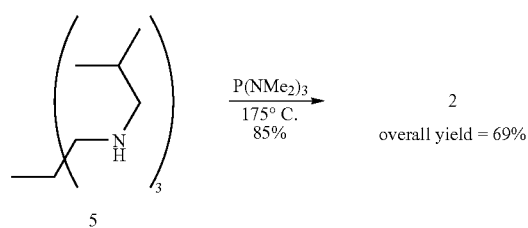

The coupling of the commercially available aza-crown ether 1-aza-15-crown-5 (10) with aryl chlorides was investigated. It was established that a variety of aryl chlorides can be coupled with 1-aza-15-crown-5 using 1 mol % $Pd_2(dba)_3$ and 4 mol % ligand 1 in toluene at 100° C. in the presence of NaO-t-Bu as the base (Scheme 2).

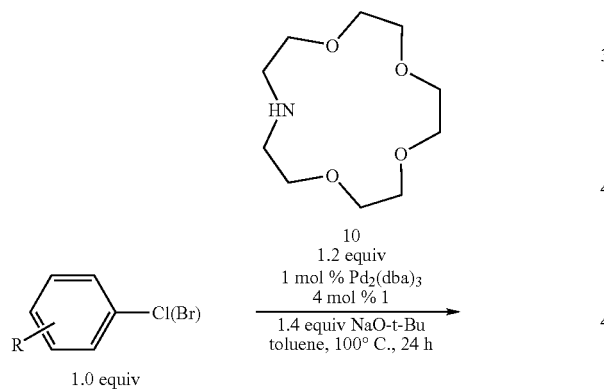

Scheme 2. $Pd_2(dba)_3$/1-Catalyzed Synthesis of N-Aryl-Aza-Crown Ethers

Aryl chlorides possessing an ester, nitro, or nitrile R-group did not fare well in this approach. For these substrates, however, conditions developed using ligand 2 in the presence of the mild base $Cs_2CO_3$ proved effective (Scheme 3).

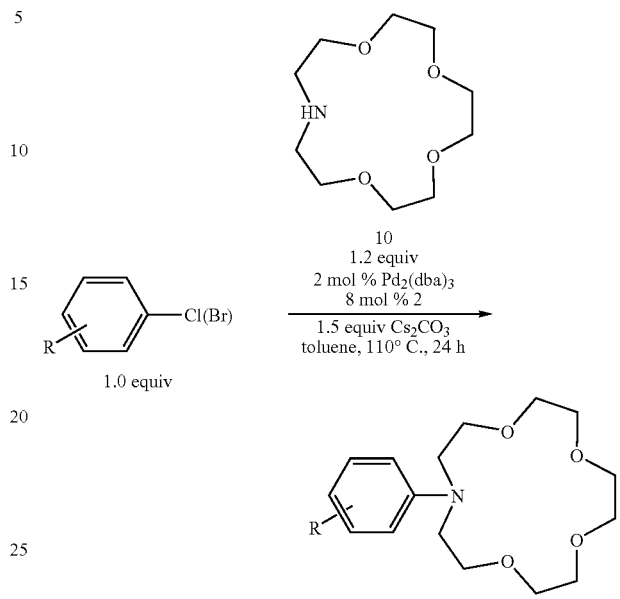

Scheme 3. $Pd_2(dba)_3$/2-Catalyzed Synthesis of N-Aryl-Aza-Crown Ethers Processing Base-Sensitive Functional Groups The potential and scope of this methodology is illustrated in Table 1 by the reaction of a variety of aryl chlorides and bromides with 1-aza-15-crown-5. Electronically diverse aryl chlorides as well as bromides can be coupled successfully in good to excellent yields with aza-crown ether 10. Using the $Pd_2(dba)_3$/1 catalyst system (2 mol % Pd), electron-poor 4-chlorobenzotrifluoride afforded the desired product in 86% yield (entry 1). Electron-neutral 4-chlorotoluene also reacted efficiently (80% product yield, entry 5). Electron-rich 4-chloroanisole also functioned as a substrate, providing the desired N-aryl-aza-crown ether in moderate yield (50%, entry 7). The meta-substituted aryl chloride, 3-chloroanisole afforded a 66% product yield (entry 6). Notably, 2-chloropyridine and less reactive 3-chloropyridine were also successfully coupled (entries 8 and 9). The coupling shown in entry 9 is particularly impressive, because to date, no catalyst system has been reported that is effective to couple of 3-halopyridines with aza-crown ethers. Under these conditions, electron-neutral and electron-rich aryl bromides also could be coupled in good yields (entries 11-13).

TABLE 1

$Pd_2(dba)_3$/1 or 2-Catalyzed Synthesis of N-Aryl-Aza-Crown Ethers

| entry | aryl halide | ligand | mol % Pd | base | yield (%)[a] |
|---|---|---|---|---|---|
| 1 | $F_3C$—⟨⟩—Cl | 1 | 2 | NaO-t-Bu | 80[b] |
| 2 | $MeO_2C$—⟨⟩—Cl | 2 | 4 | $Cs_2CO_3$ | 73[c] |

TABLE 1-continued

Pd$_2$(dba)$_3$/1 or 2-Catalyzed Synthesis of N-Aryl-Aza-Crown Ethers

| entry | aryl halide | ligand | mol % Pd | base | yield (%)[a] |
|---|---|---|---|---|---|
| 3 | 4-O$_2$N-C$_6$H$_4$-Cl | | 2 | 4 | Cs$_2$CO$_3$ | 81[c] |
| 4 | 4-NC-C$_6$H$_4$-Cl | | 2 | 4 | Cs$_2$CO$_3$ | 56[c] |
| 5 | 4-Me-C$_6$H$_4$-Cl | | 1 | 2 | NaO-t-Bu | 80[b] |
| 6 | 3-MeO-C$_6$H$_4$-Cl | | 1 | 2 | NaO-t-Bu | 66[b] |
| 7 | 4-MeO-C$_6$H$_4$-Cl | | 1 | 2 | NaO-t-Bu | 50[b] |
| 8 | 2-chloropyridine | | 1 | 2 | NaO-t-Bu | 76[b] |
| 9 | 3-chloropyridine | | 1 | 2 | NaO-t-Bu | 51[b] |
| 10 | 4-O$_2$N-C$_6$H$_4$-Br | | 2 | 2 | Cs$_2$CO$_3$ | 87[c] |
| 11 | 3,5-Me$_2$-C$_6$H$_3$-Br | | 1 | 2 | NaO-t-Bu | 82[b] |
| 12 | 3-MeO-C$_6$H$_4$-Br | | 1 | 2 | NaO-t-Bu | 68[b] |
| 13 | 4-MeO-C$_6$H$_4$-Br | | 1 | 2 | NaO-t-Bu | 60[b] |

[a]Isolated yields (average of two runs).
[b]For reaction conditions, see Scheme 2.
[c]For reaction conditions, see Scheme 3.

As previously discussed, the Pd$_2$(dba)$_3$/2 catalyst system was employed (4 mol % Pd) in the presence of the weak base Cs$_2$CO$_3$ for substrates with base-sensitive functional groups. Thus, methyl-3-chlorobenzoate (73%, entry 2), 4-chloronitrobenzene (81%, entry 3), 4-chlorobenzonitrile (56%, entry 4), and 4-bromonitrobenzene (87%, entry 10) were all aminated under these standard conditions. For the reaction of 4-bromonitrobenzene, however, 2 mol % of Pd was sufficient for the coupling to occur in high yield. Ortho-substituted aryl chlorides did not couple with 1-aza-15-crown-5 to an appreciable extent and ortho-substituted aryl bromides provided only trace amounts of products.

Methodology based on the Pd$_2$(dba)$_3$/1 catalyst system has been extended to the arylation of a second aza-crown ether, namely, 1-aza-18-crown-6 (11) and the results are summarized in Table 2. Using unactivated and deactivated aryl chlorides, bromides, and iodides, yields obtained were in the range of 51-55% (entries 1-4). For an aryl iodide, only 1 mol % of Pd was used.

TABLE 2

Pd₂(dba)₃/1-Catalyzed Coupling of Aryl Halides with 1-Aza-18-crown-6

| entry | aryl halide | mol % Pd | yield (%)[a] |
|---|---|---|---|
| 1 | MeO—C₆H₄—Cl | 2 | 51 |
| 2 | Me—C₆H₄—Cl | 2 | 52 |
| 3 | MeO—C₆H₄—Br | 1.8 | 54 |
| 4 | MeO—C₆H₄—I | 1 | 55 |

[a]Isolated yields (average of two runs).

Conclusions

The synthesis of various N-aryl-aza-crown ethers was readily achieved via palladium-catalyzed amination of aryl chlorides, bromides, and iodides in which the catalyst system comprises Pd₂(dba)₃ and one of the bicyclic triaminophosphine ligands 1 or 2, the choice depending on the nature of the aryl substrate. Using this approach, the reaction is tolerant of a wide variety of functional groups. This protocol is the first reported for coupling aryl chlorides with aza-crown ethers.

Experimental

General methods: Pd₂(dba)₃, NaO-t-Bu, and Cs₂CO₃ were purchased from Aldrich and used without further purification. Toluene was collected from a Grubbs-type solvent purification system. All other reagents were commercially available and were used as received. Ligands 1 was prepared according to previously reported procedures (Kisanga, P. B.; Verkade, J. G. *Tetrahedron* 2001, 57, 467), although 1 is commercially available from Aldrich and Strem Chemicals. For convenience, stock solutions of 1 and 2 in toluene (2 mM) were prepared and stored under argon. All reactions were performed under an atmosphere of argon in oven-dried glassware. $^1$H and $^{13}$C NMR spectra were recorded at 300 and 75.5 MHz, respectively, unless otherwise noted. Elemental analyses were performed by Desert Analytics (Tucson, Ariz., USA). Mass spectra were recorded on a Kratos MS 50 instrument. The yields reported are isolated yields and are the average of two runs.

Synthesis of Bicyclic Ligand 2.

Isobutyryl chloride (80.0 mmol) in 20 mL of dry CH₂Cl₂ was added dropwise to a mixture of tris(2-aminomethyl) ethane 4 (20.0 mmol) and triethylamine (80.0 mmol) in 40 mL of dry CH₂Cl₂ at 0° C. The mixture was stirred at room temperature overnight. After filtering the precipitate that formed, the filtrate was concentrated on a rotary evaporator and then diluted with water (30 mL). The product was extracted with EtOAc (3×100 mL) and then the organic layers were combined, dried (Na₂SO₄) and the solvent was removed under reduced pressure to afford a slurry which was used in the next step without further purification. The slurry (18.0 mmol, as crude product) in 50 mL of dry THF was added dropwise to a solution of LiAlH₄ (126.0 mmol) in 200 mL of dry THF over a period of 30 min. The mixture was then refluxed for three days after which it was cooled to 0° C. Fifty mL of a 10% KOH solution in water was then added and the mixture was again heated to reflux for 4 hours. The white precipitate that had formed was filtered, washed with hot THF (3×100 mL) and the filtrates were then combined. THF was removed under reduced pressure and the crude product obtained was distilled under vacuum to afford 5 in 81% yield from 4 as a colorless oil (bp: 78-80° C./200 mTorr). $^1$H NMR (CDCl₃) δ 0.86 (d, 21H, J=6.7 Hz), 1.53 (broad s, 3H), 1.65 (m, 3H), 2.33 (d, 6H, J=6.6 Hz), 2.50 (s, 6H); $^{13}$C NMR (CDCl₃) δ 20.9, 22.8, 28.3, 38.4, 58.6, 59.3. Anal. Calcd. for C₁₇H₃₉N₃: C, 71.58; H, 13.68; N, 14.74. Found: C, 71.71; H, 13.30; N, 14.66.

tris(2-iso-Butylaminomethyl)ethane 5 (8.8 mmol) and P(NMe₂)₃ (9.0 mmol) were charged to a 50 mL flask under Argon. The flask was placed in a 175° C. oil bath and the reaction mixture was stirred for three days at that temperature. The crude material obtained was distilled under vacuum to afford 2 in 85% yield (overall yield from 4, 69%) as a colorless oil (bp: 80-82° C./200 mTorr). $^1$H NMR (C$_6$D$_6$) δ 0.58 (s, 3H), 0.88 (d, 18H, J=6.6 Hz), 1.70 (m, 3H), 2.46 (d, 6H, J=3.1 Hz), 2.62 (m, 6H). $^{13}$C NMR (C$_6$D$_6$) δ 20.4, 22.6, 27.0 (d, J=11.0 Hz), 34.3 (d, J=1.6 Hz), 59.8 (d, J=4.0 Hz), 61.6 (d, J=25.0 Hz). $^{31}$P NMR (C$_6$D$_6$) δ 81.6. Anal. Calcd. for C$_{17}$H$_{36}$N$_3$P: C, 65.17; H, 11.50; N, 13.42. Found: C, 64.27; H, 11.70; N, 13.64.

General Procedure for the Coupling of Aryl Halides with Aza-crown ethers using the Pd$_2$(dba)$_3$/1 or Pd$_2$(dba)$_3$/2 catalyst system (Tables 1 and 2): An oven-dried Schlenk flask equipped with a magnetic stirring bar was charged with Pd$_2$(dba)$_3$ (0.5-2 mol %, see Tables 1 and 2), an appropriate aza-crown ether (1.2 mmol), and NaO-t-Bu (1.4 mmol) or Cs$_2$CO$_3$ (1.5 mmol) inside a glovebox. If the aryl halide (1.0 mmol) was a solid, it was also added at this time. The flask was capped with a rubber septum and removed from the glove box. Ligand 1 or 2 (2-8 mol %) was then added via syringe from a stock solution (2 mM in toluene). Aryl halide (if a liquid, 1.0 mmol) and toluene (3 mL) were then successively added via syringe. The reaction mixture was heated at the temperature indicated (see Tables 1 and 2) for 24 hours. The mixture was then cooled to room temperature, adsorbed onto silica gel and then purified by column chromatography using initially 10% ethyl acetate/hexanes and then ethyl acetate as eluents.

Spectroscopic Data for Unknown Compounds:

N-(3-Carbomethoxyphenyl)-1-aza-15-crown-5 (Table 1, entry 2). $^1$H NMR (300 MHz, CDCl$_3$): δ 7.30-7.19 (m, 3H), 6.85-6.82 (m, 1H), 3.86 (s, 3H), 3.76-3.58 (m, 20H). $^{13}$C NMR (75 MHz, CDCl$_3$): δ 167.9, 147.8, 131.3, 129.4, 117.0, 116.0, 112.3, 71.5, 70.4, 70.3, 68.6, 52.7, 52.2. HRMS m/z Calcd for C$_{18}$H$_{27}$NO$_6$: 353.18384. Found: 353.18430. Anal. Calcd for C$_{18}$H$_{27}$NO$_6$: C, 61.19; H, 7.65. Found: C, 61.34; H, 7.81.

N-(2-Pyridinyl)-1-aza-15-crown-5 (Table 1, entry 8). $^1$H NMR (300 MHz, CDCl$_3$): δ 8.05 (d, J=3.5 Hz, 1H), 7.34 (t, J=7.1 Hz, 1H), 6.49-6.42 (m, 2H), 3.72-3.57 (m, 20H). $^{13}$C NMR (75 MHz, CDCl$_3$): δ 157.8, 148.0, 137.2, 111.6, 106.0, 71.4, 70.4, 70.2, 69.3, 51.2. HRMS m/z Calcd for C$_{15}$H$_{24}$N$_2$O$_4$: 296.17361. Found: 296.17410. Anal. Calcd for C$_{15}$H$_{24}$N$_2$O$_4$: C, 60.81; H, 8.11. Found: C, 60.67; H, 8.31.

N-(3-Pyridinyl)-1-aza-15-crown-5 (Table 1, entry 9). $^1$H NMR (400 MHz, CDCl$_3$): δ 8.08-8.05 (m, 1H), 7.90 (d, J=4.3 Hz, 1H), 7.09-7.06 (m, 1H), 6.94-6.92 (m, 1H), 3.74-3.55 (m, 20H). $^{13}$C NMR (100 MHz, CDCl$_3$): δ 143.7, 137.3, 134.2, 123.8, 118.2, 71.5, 70.5, 70.2, 68.4, 52.5. HRMS m/z Calcd for C$_{15}$H$_{24}$N$_2$O$_4$: 296.17361. Found: 296.17410. Anal. Calcd for C$_{15}$H$_{24}$N$_2$O$_4$: C, 60.81; H, 8.11. Found: C, 60.98; H, 7.97.

N-(4-Methoxyphenyl)-1-aza-18-crown-6 (Table 2, entries 1, 3, and 4). $^1$H NMR (300 MHz, CDCl$_3$): δ 6.82-6.70 (m, 4H), 3.74-3.56 (m, 27H). $^{13}$C NMR (75 MHz, CDCl$_3$): δ 151.8, 142.4, 115.1, 114.4, 71.03, 70.99, 70.8, 69.0, 56.0, 52.4. HRMS m/z Calcd for C$_{19}$H$_{31}$NO$_6$: 369.21514. Found: 369.21580. Anal. Calcd for C$_{19}$H$_{31}$NO$_6$: C, 61.79; H, 8.40. Found: C, 61.63; H, 8.33.

N-(4-Methylphenyl)-1-aza-18-crown-6 (Table 2, entry 2). $^1$H NMR (300 MHz, CDCl$_3$): δ 7.02 (d, J=8.4 Hz, 2H), 6.62 (d, J=8.5 Hz, 2H), 3.70-3.56 (m, 24H), 2.23 (s, 3H). $^{13}$C NMR (75 MHz, CDCl$_3$): δ 146.0, 130.0, 125.2, 112.1, 71.1, 71.08, 71.0, 70.9, 69.1, 51.7, 20.4. HRMS m/z Calcd for C$_{19}$H$_{31}$NO$_5$: 353.22022. Found: 353.22100. Anal. Calcd for C$_{19}$H$_{31}$NO$_5$: C, 64.59; H, 8.78. Found: C, 64.67; H, 8.67.

Example 2

Application of a New Bicyclic Triaminophosphine Ligand in Pd-Catalyzed Buchwald-Hartwig Amination Reactions of Aryl Chlorides, Bromides and Iodides The new bicyclic triaminophosphine ligand P(i-BuNCH$_2$)$_3$CMe (2) has been synthesized in three steps from commercially available materials and its efficacy in palladium-catalyzed reactions of aryl halides with a wide variety of amines has been demonstrated. Electron-poor, electron-neutral, and electron-rich aryl bromides, chlorides, and iodides participated in the process. The reactions encompassed aromatic amines (primary or secondary) and secondary amines (cyclic or acyclic). The weak base Cs$_2$CO$_3$ can also be employed with ligand 2, allowing a variety of functionalized substrates (e.g., those containing esters and nitro groups) to be used in the present amination reaction. This ligand provides a remarkably general, efficient, and mild palladium catalyst for aryl iodide amination. Although 2 is slightly air and moisture sensitive, easy procedures can be adopted that avoid the need of a glove box. Comparisons of the efficacy of 2 in these reactions with that of the proazaphosphatrane P(i-BuNCH$_2$CH$_2$)$_3$N (1) reveal that in addition to the opportunity for transannulation in 1 (but not in 2), other significant stereoelectronic contrasts exist between these two ligands which help account for differences in the activities of the Pd/1 and Pd/2 catalytic systems.

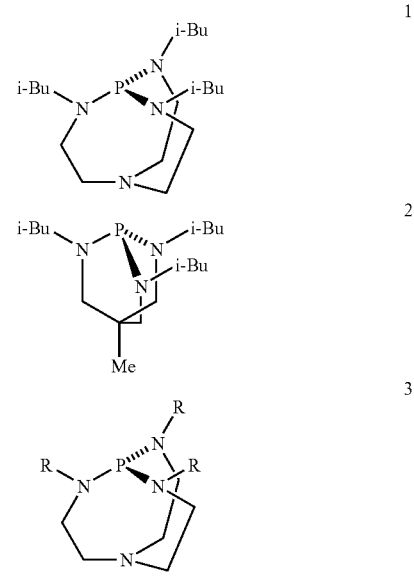

In recent years proazaphosphatranes of general formula 3 have been shown to be exceedingly potent catalysts, promoters, and strong nonionic stoichiometric bases that facilitate a variety of useful organic transformations (Verkade, J. G. Top. Curr. Chem. 2002, 233, 1). More recently, Verkade discovered that commercially available 1 is a highly active ligand in Suzuki and Buchwald-Hartwig amination reactions of aryl halides, including those of aryl chlorides. For Suzuki coupling reactions, see Urgaonkar, S.; Nagarajan, M.; Verkade, J. G. Tetrahedron Lett. 2002, 43, 8921; for Buchwald-Hartwig amination reactions of aryl halides, see Urgaonkar, S.; Nagarajan, M.; Verkade, J. G. *J. Org. Chem.* 2003, 68, 452; and Urgaonkar, S.; Nagarajan, M.; Verkade, J. G. *Org. Lett.* 2003, 5, 815.

It is believed that the unusually high activity of 1 in Suzuki and Buchwald-Hartwig amination reactions was due primarily to a) the electron-donating capability of the three planar $PN_3$ nitrogens, b) a desirable degree of bulk provided by the iso-butyl groups, and c) potential transannulation from the bridgehead nitrogen's lone pair to phosphorus. Thus in contrast, acyclic triaminophosphines [e.g., $P(NMe_2)_3$ or $P(Ni-Bu_2)_3$] were shown to be very ineffective ligands in amination reactions partly because the phosphorus in these triaminophosphines is not sufficiently electron-rich. This is believed to be due to a departure of the conformation of these molecules from a $C_3V$ arrangement of the $P(NC_2)_3$ moiety in which the unhybridized lone pair orbital on each nitrogen lies tangential to a circle whose plane is perpendicular to and contains the three-fold axis at its center. See Molloy, K. G.; Petersen, J. L. *J. Am. Chem. Soc.* 1995, 117, 7696; Xi, S. K.; Schmidt, H.; Lensink, C.; Kim, S.; Wintergrass, D.; Daniels, L. M.; Jacobson, R. A.; Verkade, J. G. *Inorg. Chem.* 1990, 29, 2214; Socol, S. M.; Jacobson, R. A.; Verkade, J. G. *Inorg. Chem.* 1984, 23, 88; Romming, C.; Songstad, J. *Acta Chem. Scand., Ser. A* 1980, 34, 365; and Romming, C.; Songstad, J. *Acta Chem. Scand., Ser. A* 1979, 33, 187. For a discussion of the electronic structure of tris(dialkylamino)phosphines, see: Cowley, A. H.; Lattman, M.; Stricklen, P. M.; Verkade, J. G. *Inorg. Chem.* 1982, 21, 543.

This Example presents the utility of 2 in Pd-catalyzed Buchwald-Hartwig amination reactions of aryl chlorides, bromides and iodides.

Results and Discussion

Catalytic activity of 2 in aryl bromide amination reactions. The initial test of the efficacy of 2 in Pd-catalyzed amination reactions involved aryl bromides with NaO-t-Bu as the base. Conditions developed for the amination reactions that employed 1 as the ligand also worked for ligand 2. It is noted that reactions were also performed with the trimethyl and tri-iso-propyl analogues of ligand 1. For the reaction shown in Table 3, entry 6, the trimethyl analogue provided less than 20% yield whereas tri-iso-propyl analogue yielded 62% of the coupled product using 2 mol % Pd in both cases. The general reaction conditions for the coupling reaction are described in Scheme 4 and results are provided in Table 3.

Scheme 4

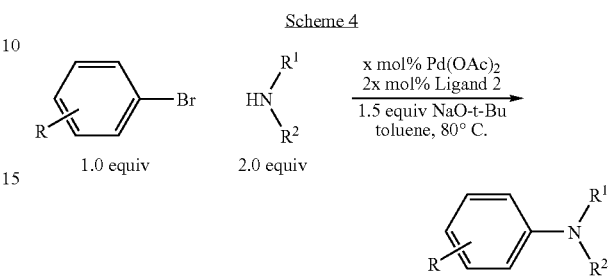

For the majority of substrates, 0.5 mol % Pd was sufficient to achieve high yields of arylamines, and most of these reactions were completed in less than 20 hours. No attempts were made to optimize reaction times. Electron-poor, electron-neutral, and electron-rich aryl bromides, including, bromopyridines, were readily aminated with the $Pd(OAc)_2/2$ catalyst system. Primary anilines with ortho-substituents and secondary anilines were efficiently coupled at 80° C.

As was the case with the $Pd(OAc)_2/1$ catalyst system, amination reactions of highly sterically hindered substrates using $Pd(OAc)_2/2$ also proceeded exceedingly well (entry 13, Table 3). Hydrodehalogenation side products were detectable in most cases by TLC. The $Pd(OAc)_2/2$ catalyst system was also effective for the arylation of cyclic secondary amines (entries 2, 6, 7 and 14, Table 3). Di-n-butylamine (a member of a normally difficult class of substrates) was also cleanly coupled, giving the desired product in very good to acceptable yields. For this class of amines, 2 mol % Pd was needed (entries 3, 8 and 15, Table 3).

TABLE 3

Pd/2-Catalyzed Amination of Aryl and Heteroaryl Bromides[a]

| Entry | Bromide | Amine | mol % Pd | Product | Yield (%)[b] |
|---|---|---|---|---|---|
| 1 | NC—⟨⟩—Br | HN(Me)(Ph) | 0.5 | NC—⟨⟩—N(Me)(Ph) | 96 |
| 2 | t-Bu—⟨⟩—Br | HN⟨morpholine⟩ | 0.5 | t-Bu—⟨⟩—N⟨morpholine⟩ | 93 |
| 3 | " | $Bu_2NH$ | 2 | t-Bu—⟨⟩—N(Bu)(Bu) | 95 |
| 4 | " | $Ph_2NH$ | 1 | t-Bu—⟨⟩—N(Ph)(Ph) | 94[c] |

TABLE 3-continued

Pd/2-Catalyzed Amination of Aryl and Heteroaryl Bromides[a]

| Entry | Bromide | Amine | mol % Pd | Product | Yield (%)[b] |
|---|---|---|---|---|---|
| 5 | " | 4-MeO-C6H4-NH2 | 2 | t-Bu-C6H4-NH-C6H4-OMe | 78[c] |
| 6 | 4-MeO-C6H4-Br | morpholine | 1 | 4-MeO-C6H4-morpholine | 92 |
| 7 | " | piperidine | 0.5 | 4-MeO-C6H4-piperidine | 67 |
| 8 | " | Bu2NH | 2 | 4-MeO-C6H4-NBu2 | 73 |
| 9 | " | Ph2NH | 2 | 4-MeO-C6H4-NPh2 | 95[c] |
| 10 | " | MeN(H)Ph | 0.5 | 4-MeO-C6H4-N(Me)Ph | 92 |
| 11 | " | 4-Me-C6H4-NH2 | 2 | 4-MeO-C6H4-NH-C6H4-4-Me | 77[c] |
| 12 | " | 2,6-Me2-C6H3-NH2 | 2 | 4-MeO-C6H4-NH-C6H3-2,6-Me2 | 93 |
| 13 | 2-Br-1,3,5-Me3-C6H2 | 2,6-Me2-C6H3-NH2 | 0.5 | 2,4,6-Me3-C6H2-NH-C6H3-2,6-Me2 | 96 |
| 14 | 2-Br-pyridine | morpholine | 0.5 | 2-(morpholino)pyridine | 93 |
| 15 | " | Bu2NH | 2 | 2-(NBu2)pyridine | 88 |

TABLE 3-continued

Pd/2-Catalyzed Amination of Aryl and Heteroaryl Bromides[a]

| Entry | Bromide | Amine | mol % Pd | Product | Yield (%)[b] |
|---|---|---|---|---|---|
| 16 | " | Ph₂NH | 4 | 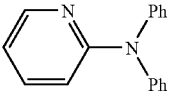 | 87[c,d] |
| 17 | 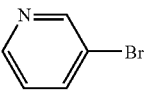 |  | 5 | 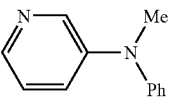 | 84[d] |

[a]Conditions: 1.0 equiv of aryl bromide, 1.2 equiv of amine, 1.5 equiv of NaO-t-Bu, cat. Pd(OAc)₂, cat. ligand 2 (2L/Pd), 3 mL of toluene, 80° C., 15-20 hours. Reaction times not optimized.
[b]Isolated yields.
[c]Reaction was performed at 100° C.
[d]Pd₂(dba)₃ used in place of Pd(OAc)₂.

When ligand 1 was employed, reactions of acyclic secondary amines proceeded in only moderate yields (57-70%) and required 5 mol % Pd (Urgaonkar, et al. *J. Org. Chem.* 2003, 68, 452). Unfortunately, long-chain (n-hexylamine) or branched primary aliphatic amines (cyclohexylamine) did not react cleanly under the instant conditions.

Although primary anilines without an ortho-substituent reacted poorly using the 2/Pd catalyst system at 80° C., a reaction temperature of 100° C. allowed efficient coupling of this class of anilines. For example, the reaction of 4-bromoanisole with p-toluidine proceeded to completion using 2 mol % Pd(OAc)₂ and 4 mol % 2 at 100° C., affording the desired product in 77% yield (entry 11, Table 3). Similarly, 4-tert-butylbromobenzene coupled with p-anisidine to give a 78% yield of product (entry 5, Table 3).

Although the above protocol is effective, it involves the use of NaO-t-Bu as the base, thus rendering the conditions ineffective for aryl halides containing base-sensitive functional groups. After surveying a range of bases, if was found that the weaker base Cs₂CO₃ could also be employed in the presence of the Pd/2 catalyst system, and examples of amination reactions demonstrating the use of this base are shown in Table 4. In most cases these reactions proceeded successfully at 80° C. with 1 mol % Pd(OAc)₂ and 2 mol % 2. By contrast, alkylphosphine catalysts [biphenyl- or ferrocenyl-based, or P(t-Bu)₃] generally require heating up to 100° C. for the amination of functionalized aryl bromides (Kataoka, N.; Shelby, Q.; Stambuli, J. P.; Hartwig, J. F. *J. Org. Chem.* 2002, 67, 5553).

TABLE 4

Pd(OAc)₂/2-Catalyzed Amination of Functionalized Aryl Bromides[a]

| Entry | Bromide | Amide | Product | Yield (%)[b] |
|---|---|---|---|---|
| 1 | 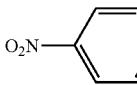 | 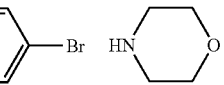 | 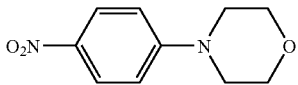 | 95 |
| 2 | 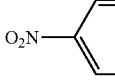 |  | 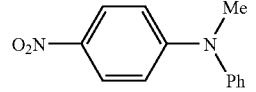 | 97 |
| 3 | 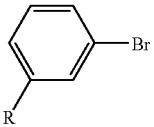 | 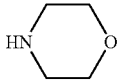 | 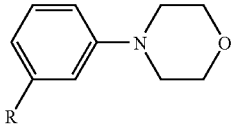 | 92[c] |
| 4 | 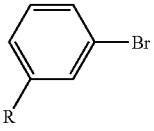 | 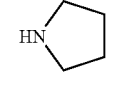 | 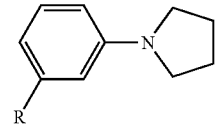 | 42[c] |
| 5 |  |  | 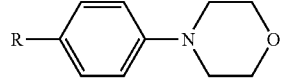 | 85[c] |

TABLE 4-continued

Pd(OAc)$_2$/2-Catalyzed Amination of Functionalized Aryl Bromides[a]

| Entry | Bromide | Amide | Product | Yield (%)[b] |
|---|---|---|---|---|
| 6 | 4-t-Bu-C$_6$H$_4$-Br | 3-NO$_2$-C$_6$H$_4$-NH$_2$ | 4-t-Bu-C$_6$H$_4$-NH-C$_6$H$_4$-3-NO$_2$ | 61[d] |

[a]Conditions: 1.0 equiv of aryl iodide, 1.2 equiv of amine, 1.5 equiv of Cs$_2$CO$_3$, 1.0 mol % Pd(OAc)$_2$, 2.0 mol % ligand 2 (2L/Pd), 3 mL of toluene, 80° C., 15-20 hours. Reaction times not optimized.
[b]Isolated yields.
[c]R = CO$_2$Me.
[d]Reaction was performed at 100° C.

Catalytic activity of 2 in aryl chloride amination reactions. The utilization of aryl chlorides in Pd-catalyzed cross-coupling reactions is important from a commercial standpoint. The results of investigations of such couplings using the Pd/2 catalyst system are summarized in Table 5. A higher catalyst loading (4 mol % Pd) and a reaction temperature of 110° C. was needed to drive the reactions to completion. In a control experiment, the reaction of activated 4-chloronitrobenzene with morpholine in toluene at 110° C. gave no desired product in the presence of CS$_2$CO$_3$. A similar experiment conducted with 4 mol % of Pd(OAc)$_2$ without any added ligand resulted in the formation of only a trace amount of product after 36 hours.

Among the solvents tested (toluene, THF, dioxane, and DME) toluene was found to be the most effective. Either Pd(OAc)$_2$ or Pd$_2$(dba)$_3$ can be used as the palladium(0) precursor. As expected, the best yields were obtained with aryl chlorides possessing electron-withdrawing groups, but electron-neutral and electron-rich aryl chlorides provided good to moderate yields of desired product. Cyclic secondary amines, secondary anilines, primary anilines, and diphenyl amine participated well in the amination process.

TABLE 5

Pd/2-Catalyzed Amination of Aryl Chlorides[a]

| Entry | Chloride | Amine | Product | Yield (%)[b] |
|---|---|---|---|---|
| 1 | 4-NC-C$_6$H$_4$-Cl | morpholine | 4-NC-C$_6$H$_4$-morpholine | 91[d] |
| 2 | " | HN(Me)Ph | 4-NC-C$_6$H$_4$-N(Me)Ph | 93[c] |
| 3 | " | 4-Me-C$_6$H$_4$-NH$_2$ | 4-NC-C$_6$H$_4$-NH-C$_6$H$_4$-4-Me | 97[c] |
| 4 | 4-O$_2$N-C$_6$H$_4$-Cl | 4-MeO-C$_6$H$_4$-NH$_2$ | 4-O$_2$N-C$_6$H$_4$-NH-C$_6$H$_4$-4-OMe | 97[c] |

TABLE 5-continued
Pd/2-Catalyzed Amination of Aryl Chlorides[a]
| Entry | Chloride | Amine | Product | Yield (%)[b] |
|---|---|---|---|---|
| 5 | " | Ph$_2$NH | 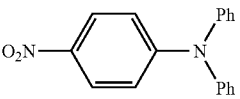 | 92[c] |
| 6 | " | 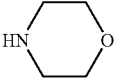 | 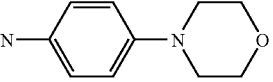 | 97[c] |
| 7 | 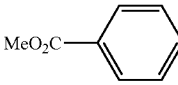 | 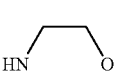 | 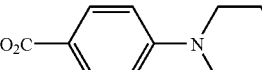 | 98[c,d] |
| 8 | " | 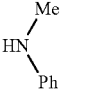 | 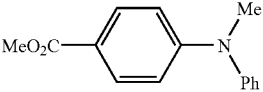 | 85[c] |
| 9 | 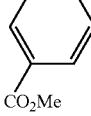 | 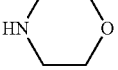 | 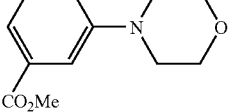 | 77[c] |
| 10 | " | 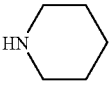 | 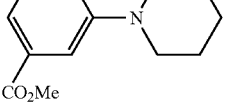 | 70[c] |
| 11 | " | 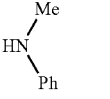 | 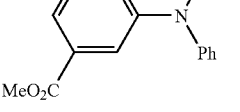 | 92[c] |
| 12 | 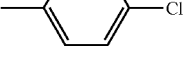 | 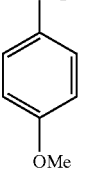 | 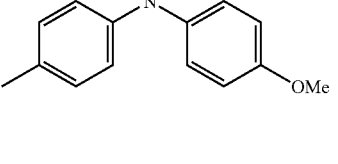 | 77[c] |
| 13 | " | 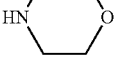 | 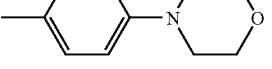 | 70 |
| 14 | 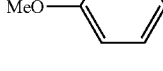 | 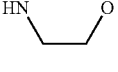 | 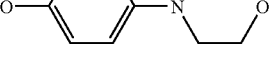 | 52 |
| 15 |  | 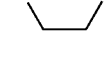 | 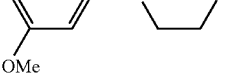 | 55 |

TABLE 5-continued

Pd/2-Catalyzed Amination of Aryl Chlorides[a]

| Entry | Chloride | Amine | Product | Yield (%)[b] |
|---|---|---|---|---|
| 16 | " | (piperidine, HN) | 3-OMe-C6H4-piperidine | 64[c] |
| 17 | " | 4-methylaniline (NH2) | 3-OMe-C6H4-NH-C6H4-4-Me | 69[c] |
| 18 | 2-chloropyridine | morpholine | 2-(morpholino)pyridine | 87[c] |
| 19 | 4-chloropyridine·HCl | morpholine | 4-(morpholino)pyridine | 85[d] |
| 20 | " | HN(Me)Ph | 4-pyridyl-N(Me)Ph | 84[d] |

[a]Conditions: 1.0 equiv of aryl chloride, 1.2 equiv of amine, 1.5 equiv of NaO-t-Bu, 2.0 mol % $Pd_2(dba)_3$, 8.0 mol % ligand 2 (2 L/Pd), 3 mL of toluene, 110° C., 24 hours. Reaction times not optimized.
[b]Isolated yields.
[c]$Cs_2CO_3$ used in place of NaO-t-Bu.
[d]$Pd(OAc)_2$ used in place of $Pd_2(dba)_3$.

Catalytic activity of 2 in aryl iodide amination reactions. Although more reactive, aryl iodides usually provide lower yields than their bromide counterparts in such reactions. Catalyst systems that have been described in the literature involve toxic additives such as 18-crown-6 (Wolfe, J. P.; Buchwald, S. L. *J. Org. Chem.* 1997, 62, 6066), higher catalyst loading (up to 5 mol %) (Driver, M. S.; Hartwig, J. F. *J. Am. Chem. Soc.* 1996, 118, 7217), lack of generality (Grasa, et al. *J. Org. Chem.* 2001, 66, 7729), and the use of the strong base (NaO-t-Bu).

It was found that the $Pd(OAc)_2/2$ catalyst system, in combination with $Cs_2CO_3$ as the base, allowed a variety of aryl iodides to couple successfully with amines at 80° C. (20-40° C. lower than the literature reports). Exceptions to this approach were the reactions where primary aniline lacking an ortho-substituent was used as a coupling partner. For unfunctionalized substrates, NaO-t-Bu was also able to function as the base. For activated aryl iodides and for one example of a deactivated aryl iodide, 0.5 mol % of Pd led to excellent yields of diarylamines (entries 1, 2, 3 and 11, Table 6). The use of 2 mol % of Pd allowed the reaction of unactivated and deactivated aryl iodides to occur in good yields (entries 6, 7, 11 and 12, Table 6).

As observed with aryl bromides, reactions of aryl iodides with primary anilines lacking an ortho-substituent required the use of a somewhat higher reaction temperature (entries 10 and 15, Table 6). Reactions of an acyclic secondary amine with aryl iodides also occurred at 80° C. (entries 4, 8 and 13, Table 6). Reactions of diphenylamine also proceeded smoothly at 100° C. with the Pd/2 catalyst system when $Cs_2CO_3$ was employed (entries 5 and 14, Table 6). As with aryl bromides, reactions of aryl iodides with primary aliphatic amines gave less satisfactory results when $Cs_2CO_3$ or NaO-t-Bu was employed as the base. Nonetheless, it appears that the Pd/2 catalyst system utilizing $Cs_2CO_3$ as the base is the most efficient, general and mild catalytic combination reported to date for the amination of aryl iodides.

TABLE 6

Pd(OAc)$_2$/2-Catalyzed Amination of Aryl Iodides[a]

| Entry | Iodide | Amine | mol % Pd | Product | Yield (%)[b] |
|---|---|---|---|---|---|
| 1 | Cl–C$_6$H$_4$–I | HN(Me)Ph | 0.5 | Cl–C$_6$H$_4$–N(Me)Ph | 96 |
| 2 | R–C$_6$H$_4$–I | HN(Me)Ph | 0.5 | R–C$_6$H$_4$–N(Me)Ph | 93[c] |
| 3 | " | morpholine | 0.5 | R–C$_6$H$_4$–N(morpholine) | 93[c] |
| 4 | " | Bu$_2$NH | 2 | R–C$_6$H$_4$–NBu$_2$ | 90[c] |
| 5 | O$_2$N–C$_6$H$_4$–I | Ph$_2$NH | 1 | O$_2$N–C$_6$H$_4$–NPh$_2$ | 80[d] |
| 6 | 4-Me-C$_6$H$_4$–I | 1,4-dioxa-8-azaspiro[4.5]decane | 2 | 4-Me-C$_6$H$_4$–N(4,4-dimethoxypiperidine) | 77 |
| 7 | " | 2,6-dimethylaniline | 2 | 4-Me-C$_6$H$_4$–NH–(2,6-Me$_2$C$_6$H$_3$) | 97 |
| 8 | " | Bu$_2$NH | 2 | 4-Me-C$_6$H$_4$–NBu$_2$ | 80 |
| 9 | 3-MeO-C$_6$H$_4$–I | morpholine | 0.5 | 3-MeO-C$_6$H$_4$–N(morpholine) | 83 |
| 10 | " | 4-methylaniline | 2 | 3-MeO-C$_6$H$_4$–NH–(4-MeC$_6$H$_4$) | 75[d] |
| 11 | 4-MeO-C$_6$H$_4$–I | morpholine | 0.5 | 4-MeO-C$_6$H$_4$–N(morpholine) | 96 |
| 12 | " | piperidine | 2 | 4-MeO-C$_6$H$_4$–N(piperidine) | 77 |

TABLE 6-continued

Pd(OAc)₂/2-Catalyzed Amination of Aryl Iodides[a]

| Entry | Iodide | Amine | mol % Pd | Product | Yield (%)[b] |
|---|---|---|---|---|---|
| 13 | " | Bu₂NH | 5 | MeO–C₆H₄–N(Bu)(Bu) | 60 |
| 14 | " | Ph₂NH | 4 | MeO–C₆H₄–N(Ph)(Ph) | 83[d] |
| 15 | " | 4-MeC₆H₄NH₂ | 2 | MeO–C₆H₄–NH–C₆H₅ | 71[d] |

[a]Conditions: 1.0 equiv of aryl iodide, 1.2 equiv of amine, 1.5 equiv of Cs₂CO₃, cat. Pd(OAc)₂, cat. ligand 2 (2L/Pd), 3 mL of toluene, 80° C., 15-20 hours. Reaction times not optimized.
[b]Isolated yields.
[c]R = CO₂Et.
[d]Reaction was performed at 100° C.

Salient features of a convenient reaction protocol. Although ligand 2 is slightly moisture and air-sensitive, procedures can be adopted that avoid the need for a glove box. A stock solution of 2 was prepared in toluene, and the appropriate amount was collected using a syringe. NaO-t-Bu and Cs₂CO₃ were stored inside the glove box and were removed (in small amounts) to the outside just before the use. Thus, for all the reactions described herein, aryl halide (if solid), amine (if solid), base and palladium acetate were weighed in air in a Schlenk flask. The flask was then evacuated and purged with argon three times. Ligand 2 was then added via syringe and also aryl halides and amines (if liquids). However, it was determined that the order of addition of reagents was not important.

In summary, the new bicyclic triaminophosphine ligand 2, which was synthesized in three facile steps, generates a very active and broadly useful Pd catalyst system for Buchwald-Hartwig amination reactions. Couplings of an electronically diverse array of aryl halides with amines are realized in good to excellent yields. In addition, the use of Cs₂CO₃ in the presence of ligand 2 in these reactions permits aryl chlorides, bromides and iodides with base-sensitive functional groups to be aminated efficiently. It appears that though the basicity of 2 is greater than that of untransannulated 1 this relationship can be reversed on coordination of these ligands in their respective Pd(II) oxidative addition intermediates arising from aryl halides. Although it has been shown that significant versatility can be achieved in the amination of aryl bromides and iodides using the Pd/2 catalyst system, there are limitations to our protocol. Thus aminations of aryl chlorides require higher catalyst loading and a reaction temperature of 110° C., and primary alkyl amines (normal or branched chain) do not function well as reagents.

Experimental Section

General Considerations: All reactions were performed under an atmosphere of argon in oven-dried glassware. Toluene was collected from a Solvent Purification System and stored over 4 Å molecular sieves. $^1$H and $^{13}$C NMR spectra were recorded at 300 and 75.5 MHz, respectively. Thin-layer chromatography (TLC) was performed using commercially prepared 60 mesh silica gel plates and visualized with short wavelength UV light (254 nm). Silica gel 60 (9385, 230-400 mesh) was used for column chromatography. The yields reported are isolated yields and are the average of at least two runs. All commercially available reagents were used as received. For convenience, a stock solution of 2 in toluene (2 mM) was prepared and stored under argon. All compounds described in Tables 1-4 are known in the literature and were characterized by comparing their $^1$H and $^{13}$C NMR or mass spectra to the previously reported data. In all cases, the comparisons were very favorable.

Pd(OAc)₂/2-Catalyzed Amination of Aryl and Heteroaryl Bromides (Table 3). General Procedure: An oven-dried Schlenk flask equipped with a magnetic stirring bar was charged with Pd(OAc)₂ (x mol %, see Table 3) and NaO-t-Bu (1.5 mmol). Amine (1.2 mmol) and aryl bromide (1.0 mmol) were also added at this time, if they were solids. The flask was capped with a rubber septum, evacuated and then flushed with argon. This cycle was repeated three times. Ligand 2 (2x mol %, see Table 3) was then added via syringe from a stock solution. Aryl bromide (if a liquid, 1.0 mmol), amine (if a liquid, 1.2 mmol) and toluene (3 mL) were then successively added by syringe. The reaction mixture was heated at the temperature indicated in Table 3 until the starting material had been completely consumed as judged by TLC (15-20 hours). The mixture was then cooled to room temperature, adsorbed onto silica gel and then purified by column chromatography (hexanes/ethyl acetate as eluent).

Pd(OAc)₂/2-Catalyzed Amination of Functionalized Aryl Bromides (Table 4). General Procedure: An oven-dried Schlenk flask equipped with a magnetic stirring bar was charged with Pd(OAc)₂ (x mol %, see Table 4) and Cs₂CO₃ (1.5 mmol). Amine (1.2 mmol) and aryl bromide (1.0 mmol) were also added at this time, if they were solids. The flask was capped with a rubber septum, evacuated and then flushed with argon. This cycle was repeated three times. Ligand 2 (2x mol %, see Table 4) was then added via syringe from a stock solution. Aryl bromide (if a liquid, 1.0 mmol), amine (if a liquid, 1.2 mmol) and toluene (3 mL) were then successively added by syringe. The reaction mixture was heated at a temperature indicated in Table 4 until the starting material had been completely consumed as judged by TLC (15-20 hours). The mixture was cooled to room temperature, adsorbed onto silica gel and then purified by column chromatography using a mixture of hexanes and ethyl acetate as eluent.

Pd(OAc)$_2$ or Pd$_2$(dba)$_3$/2-Catalyzed Amination of Aryl chlorides (Table 5). General Procedure: An oven-dried Schlenk flask equipped with a magnetic stirring bar was charged with Pd(OAc)$_2$ or Pd$_2$(dba)$_3$ (x mol %, see Table 5) and NaO-t-Bu (1.5 mmol) or Cs$_2$CO$_3$ (1.5 mmol). Amine (1.2 mmol) and aryl chloride (1.0 mmol) were also added at this time if they were solids. The flask was capped with a rubber septum, evacuated and then flushed with argon. This cycle was repeated three times. Ligand 2 (2x mol %, see Table 5) was then added via syringe from a stock solution. Aryl chloride (if a liquid, 1.0 mmol), amine (if a liquid, 1.2 mmol) and toluene (3 mL) were then successively added by syringe. The reaction mixture was heated at 110° C. until the starting material had been completely consumed as judged by TLC (24 hours). The mixture was cooled to room temperature, adsorbed onto silica gel and then purified by column chromatography (hexanes/ethyl acetate as eluent).

Pd(OAc)$_2$/2-Catalyzed Amination of Aryl Iodides (Table 6). General Procedure: An oven-dried Schlenk flask equipped with a magnetic stirring bar was charged with Pd(OAc)$_2$ (x mol %, see Table 6) and NaO-t-Bu (1.5 mmol) or Cs$_2$CO$_3$ (1.5 mmol). Amine (1.2 mmol) and aryl iodide (1.0 mmol) were also added at this time if they were solids. The flask was capped with a rubber septum, evacuated and then flushed with argon. This cycle was repeated three times. Ligand 2 (2x mol %, see Table 6) was then added via syringe from a stock solution. Aryl iodide (if a liquid, 1.0 mmol), amine (if a liquid, 1.2 mmol) and toluene (3 mL) were then successively added by syringe. The reaction mixture was heated at a temperature indicated in Table 6 until the starting material had been completely consumed as judged by TLC (15-20 hours). The mixture was cooled to room temperature, adsorbed onto silica gel and then purified by column chromatography (hexanes/ethyl acetate as eluent).

Example 3

Suzuki-Miyaura Cross-Coupling Reaction of Aryl Halides with Arylboronic Acids

The Suzuki-Miyaura reaction is typically co-catalyzed by alkyl phosphines. This Continued interest with triaminophosphine ligands prompted testing the efficacy of a new bicyclic triaminophosphine ligand 2 in palladium-catalyzed Suzuki-Miyaura reactions. Preliminary tests have revealed that the Pd(OAc)$_2$/2 catalyst system is highly active in the Suzuki-Miyaura reaction of aryl bromides with arylboronic acids. The results are described in Table 7 below. In a typical reaction procedure, an oven-dried Schlenk flask equipped with a magnetic stirring bar was charged with Pd(OAc)$_2$ (2 mol %), Cs$_2$CO$_3$ (2.0 mmol), arylboronic acid (1.5 mmol), aryl bromide (1.0 mmol) and ligand 2 (4 mol %). The flask was capped with a rubber septum, evacuated and then flushed with argon. This cycle was repeated three times. Toluene (3 mL) was then added by syringe. The flask was immersed in an oil bath preheated to 80° C. Upon complete consumption of the starting material (24 hours) as determined by TLC analysis, the mixture was cooled to room temperature, adsorbed onto silica gel and the desired biaryl compound was isolated by column chromatography (hexanes/ethyl acetate as eluents).

TABLE 7

Suzuki-Miyaura Cross-Coupling Catalyzed by Pd and Ligand 2[a]

| Entry | Aryl Halide | Arylboronic acid | Product | Yield (%)[b] |
|---|---|---|---|---|
| 1 | t-Bu—⟨C$_6$H$_4$⟩—Br | ⟨C$_6$H$_5$⟩—B(OH)$_2$ | t-Bu—⟨C$_6$H$_4$⟩—⟨C$_6$H$_5$⟩ | 93 |
| 2 | t-Bu—⟨C$_6$H$_4$⟩—Br | 2-Me-⟨C$_6$H$_4$⟩—B(OH)$_2$ | t-Bu—⟨C$_6$H$_4$⟩—⟨C$_6$H$_4$⟩-2-Me | 91 |
| 3 | 2-Me-⟨C$_6$H$_4$⟩—Br | ⟨C$_6$H$_5$⟩—B(OH)$_2$ | 2-Me-⟨C$_6$H$_4$⟩—⟨C$_6$H$_5$⟩ | 88 |
| 4 | NC—⟨C$_6$H$_4$⟩—Br | 2-OMe-⟨C$_6$H$_4$⟩—B(OH)$_2$ | NC—⟨C$_6$H$_4$⟩—⟨C$_6$H$_4$⟩-2-OMe | 97 |
| 5 | MeO—⟨C$_6$H$_4$⟩—Br | Cl—⟨C$_6$H$_4$⟩—B(OH)$_2$ | MeO—⟨C$_6$H$_4$⟩—⟨C$_6$H$_4$⟩—Cl | 96 |

TABLE 7-continued

Suzuki-Miyaura Cross-Coupling Catalyzed by Pd and Ligand 2[a]

| Entry | Aryl Halide | Arylboronic acid | Product | Yield (%)[b] |
|---|---|---|---|---|
| 6 | MeO—⟨⟩—Br | ⟨⟩—B(OH)$_2$ | MeO—⟨⟩—⟨⟩ | 90 |

[a]Reaction Conditions: 1.0 mmol of aryl halide, 1.5 mmol of arylboronic acid, 2.0 mmol of Cs$_2$CO$_3$, 2.0 mol % Pd(OAc)$_2$, 4.0 mol % ligand 2 (2L/Pd), 3 mL toluene, 80° C., 24 hours. Reaction times are not optimized.
[b]Isolated yields.

All publications, patents, and patent documents cited herein are incorporated by reference, as though individually incorporated by reference. The invention has been described with reference to various specific and preferred embodiments and techniques. However, it should be understood that many variations and modifications may be made while remaining within the spirit and scope of the invention.

What is claimed is:

1. A method to aminate aryl halides to provide an aryl amine comprising reacting an amine and an aryl halide in the presence of an effective amount of a palladium catalyst, a base, and a compound of formula II:

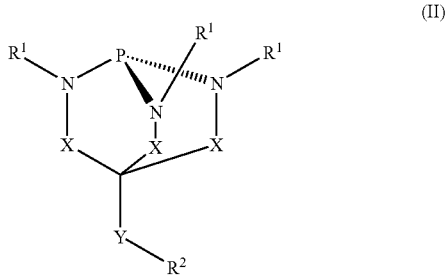

(II)

wherein
each X is independently (CH$_2$)$_n$ and each n is independently 1-3;
Y is a single bond, O, (C$_1$-C$_8$)alkylene, (C$_5$-C$_{12}$)arylene, carbonyl, oxycarbonyl, carbonyloxy, NR$_a$, or S(O)$_m$;
each R$^1$ is independently H, ethyl, propyl, isopropyl, butyl, iso-butyl, sec-butyl, tert-butyl, pentyl, 3-pentyl, hexyl, heptyl, octyl, (C$_3$-C$_8$)cycloalkyl, (C$_3$-C$_8$)cycloalkyl(C$_1$-C$_6$), (C$_1$-C$_8$)perfluoroalkyl, (C$_5$-C$_{12}$)aryl, (C$_5$-C$_{12}$)heteroaryl, (C$_5$-C$_{12}$)heterocyclyl, Si((C$_1$-C$_6$) alkyl)$_3$, Si((C$_1$-C$_6$)alkoxy)$_3$, Si((C$_5$-C$_{12}$)aryl)$_3$, or Si((C$_5$-C$_{12}$)aryloxy)$_3$;
R$^2$ is H, OR$_a$, (C$_1$-C$_8$)alkyl, (C$_3$-C$_8$)cycloalkyl, (C$_3$-C$_8$)cycloalkyl(C$_1$-C$_6$)alkyl, (C$_1$-C$_8$) perfluoroalkyl, (C$_5$-C$_{12}$)aryl, (C$_5$-C$_{12}$)heteroaryl, (C$_5$-C$_{12}$)heterocyclyl, Si((C$_1$-C$_6$)alkyl)$_3$, Si((C$_1$-C$_6$)alkoxy)$_3$, Si((C$_5$-C$_{12}$) aryl)$_3$, Si((C$_5$-C$_{12}$)aryloxy)$_3$, NHR$_a$, N(R$_a$)$_2$, halo, nitro, cyano, S(O)$_m$OR$_a$, SO$_3$H, or P(O)$_2$OR$_a$;
m is 0-2;
R$_a$ is H, (C$_1$-C$_6$)alkyl, (C$_1$-C$_6$)alkylcarbonyl, (C$_5$-C$_{12}$)aryl, or (C$_5$-C$_{12}$)aryloxy;
any alkyl is optionally substituted with one to three halo, hydroxy, nitro, cyano, (C$_5$-C$_{12}$) aryl, (C$_1$-C$_6$)alkoxy, trifluoromethyl, oxo, thioxo, or NR$_b$R$_c$ groups, wherein R$_b$ and R$_c$ are each independently hydrogen, (C$_1$-C$_6$)alkyl, or C(=O)OR$_d$ wherein R$_d$ is hydrogen or (C$_1$-C$_6$) alkyl;
any alkyl is optionally interrupted with one to three oxy, thio, amino, sulfinyl, or sulfonyl;
any alkyl is optionally partially unsaturated; and
any aryl is optionally substituted with one or more halo, hydroxyl, nitro, cyano, (C$_1$-C$_6$) alkoxy, trifluoromethyl, oxo, NR$_b$R$_c$, or C(O)OR$_d$ groups.

2. The method of claim 1 wherein each X is —CH$_2$— and each R$^1$ is ethyl, propyl, isopropyl, butyl, iso-butyl, sec-butyl, tert-butyl, pentyl, 3-pentyl, hexyl, heptyl, or octyl.

3. The method of claim 1 wherein each R$^1$ is isobutyl.

4. The method of claim 1 wherein Y is a single bond and R$^2$ is methyl.

5. The method of claim 1 wherein the palladium catalyst comprises a palladium (0) catalyst.

6. The method of claim 1 wherein an active catalytic palladium species is formed from Pd(OAc)$_2$ or Pd$_2$(dba)$_3$.

7. The method of claim 1 wherein the base is a carbonate or an alkoxide.

8. The method of claim 1 wherein the base is cesium carbonate or sodium tert-butoxide.

9. The method of claim 1 wherein the palladium catalyst is present in about 0.5 mol % to about 5 mol %, with respect to the aryl halide.

10. The method of claim 1 wherein the compound of formula II is present in about 1 mol % to about 10 mol %, with respect to the aryl halide.

11. The method of claim 1 wherein the amine and aryl halide are heated to a temperature of about 50° C. to about 120° C.

12. The method of claim 1 wherein the method is carried out in a solvent system comprising toluene.

13. The method of claim 1 wherein the amine comprises an aza-crown ether or an aryl amine.

14. The method of claim 1 wherein the aryl halide is an aryl chloride.

15. The method of claim 1 wherein the compound of formula II is

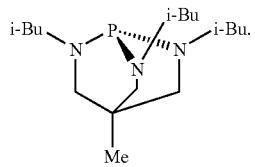

* * * * *